United States Patent
Wang et al.

(10) Patent No.: US 12,098,199 B2
(45) Date of Patent: *Sep. 24, 2024

(54) IMMUNOLOGIC EFFECTOR CELL OF TARGETED CLD18A2, AND PREPARATION METHOD AND USE THEREOF

(71) Applicant: CRAGE medical Co., Limited, Hong Kong (CN)

(72) Inventors: Huamao Wang, Shanghai (CN); Bo Song, Shanghai (CN); Xiumei Cai, Shanghai (CN)

(73) Assignee: CRAGE MEDICAL CO., LIMITED, Hong Kong (CN)

( * ) Notice: Subject to any disclaimer, the term of this patent is extended or adjusted under 35 U.S.C. 154(b) by 281 days.

This patent is subject to a terminal disclaimer.

(21) Appl. No.: 17/522,284

(22) Filed: Nov. 9, 2021

(65) Prior Publication Data

US 2022/0363751 A1    Nov. 17, 2022

Related U.S. Application Data

(63) Continuation of application No. 16/448,053, filed on Jun. 21, 2019, now Pat. No. 11,198,729, which is a continuation of application No. 15/326,974, filed as application No. PCT/CN2015/084023 on Jul. 15, 2015, now Pat. No. 10,377,822.

(30) Foreign Application Priority Data

Jul. 17, 2014   (CN) .......................... 201410341504.X

(51) Int. Cl.

| | |
|---|---|
| C07K 16/28 | (2006.01) |
| A61K 35/17 | (2015.01) |
| A61K 48/00 | (2006.01) |
| C07K 14/705 | (2006.01) |
| C07K 14/725 | (2006.01) |
| C07K 19/00 | (2006.01) |
| C12N 5/10 | (2006.01) |
| C12N 15/62 | (2006.01) |
| C12N 15/867 | (2006.01) |
| A61K 35/12 | (2015.01) |

(52) U.S. Cl.
CPC .............. *C07K 16/28* (2013.01); *A61K 35/17* (2013.01); *A61K 48/00* (2013.01); *C07K 14/7051* (2013.01); *C07K 14/70517* (2013.01); *C07K 14/70521* (2013.01); *C07K 14/70578* (2013.01); *C07K 19/00* (2013.01); *C12N 5/10* (2013.01); *C12N 15/62* (2013.01); *C12N 15/867* (2013.01); *A61K 2035/124* (2013.01); *C07K 2317/53* (2013.01); *C07K 2317/622* (2013.01); *C07K 2319/02* (2013.01); *C07K 2319/03* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 9,175,308 B2 | 11/2015 | Shiku et al. | |
| 10,377,822 B2 | 8/2019 | Wang et al. | |
| 11,198,729 B2 * | 12/2021 | Wang ........................ | C12N 5/10 |
| 2007/0186437 A1 | 8/2007 | Gasteyer et al. | |

FOREIGN PATENT DOCUMENTS

| | | |
|---|---|---|
| CN | 103483453 A | 1/2014 |
| CN | 103820393 A | 5/2014 |
| JP | 2009517354 A | 4/2009 |
| WO | WO-8909622 A1 | 10/1989 |
| WO | WO-9007861 A1 | 7/1990 |
| WO | WO-9110741 A1 | 7/1991 |
| WO | WO-9402602 A1 | 2/1994 |
| WO | WO-9633735 A1 | 10/1996 |
| WO | WO-2005113587 A2 | 12/2005 |
| WO | WO-2007059997 A1 | 5/2007 |
| WO | WO-2012038055 A1 | 3/2012 |
| WO | WO-2013051718 A1 | 4/2013 |
| WO | WO-2014075788 A1 | 5/2014 |
| WO | WO-2014180306 A1 | 11/2014 |
| WO | WO-2015113576 A1 | 8/2015 |
| WO | WO-2016008405 A1 | 1/2016 |

OTHER PUBLICATIONS

Savoldo, et al., CD28 costimulation improves expansion and persistence of chimeric antigen receptor modified T cells in lymphoma patients, J Clin Invest, May 2011, 121 (5):1822-1826.
Beatty et al. Chimeric antigen receptor T cells are vulnerable to immunosuppressive mechanisms present within the tumor microenvironment. Oncoimmunology 3(11):e970027 (2014).
Brentjens, et al. Car T Update Part 2: Challenges and Opportunities in Solid Tumors. Published by the Memorial Sloan Kettering Cancer Center, New York, NY. at https://www.mskcc.org/clinical-updates/car-update-part-2-challenges-and-opportunities-solid-tumors. 16 pages as printed. (Year: 2020).
Carpenito et al. Control of large, established tumor xenografts with genetically retargeted human T cells containing CD28 and CD137 domains. PNAS USA 106(9):3360-3365 (2009).
Cartellieri, et al., Chimeric antigen receptor-engineered T cells for immunotherapy of Cancer, J Biomed Biotechnol, 2010, 1-10. Doi : 10.1155/2010/956304.

(Continued)

*Primary Examiner* — Robert M Kelly
(74) *Attorney, Agent, or Firm* — Wilson Sonsini Goodrich & Rosati

(57) ABSTRACT

Disclosed are a chimeric antigen receptor (CAR) targeting CLD18A2, and preparation method and use thereof. The extracellular binding region of the CAR comprises a protein specifically recognizing CLD18A2. The immune effector cell modified by the CAR can be used to treat tumors such as pancreatic cancer and stomach cancer.

10 Claims, 4 Drawing Sheets
(2 of 4 Drawing Sheet(s) Filed in Color)

Specification includes a Sequence Listing.

(56) References Cited

OTHER PUBLICATIONS

Citation in opposition procedure—D1—WO2015/113576 A1 + sequence listing. Opposition by BioNTech Cell & Gene Therapies GmbH filed Jun. 4, 2020 against EP3170842 Application No. 15821331.4. Consolidated List of Cited Opposition Documents reference D1. BioNTech Cell & Gene Therapies GmbH reference D3. 134 pages.
Citation in opposition procedure—D10—English machine translation of D6. Opposition by BioNTech Cell & Gene Therapies GmbH filed Jun. 4, 2020 against EP3170842 Application No. 15821331.4. Consolidated List of Cited Opposition Documents reference D10. BioNTech Cell & Gene Therapies GmbH reference D6a. 33 pages.
Citation in opposition procedure—D11—Sadelain et al. 2013, Cancer Discovery 3: 388-398. Opposition by BioNTech Cell & Gene Therapies GmbH filed Jun. 4, 2020 against EP3170842 Application No. 15821331.4. Consolidated List of Cited Opposition Documents reference D11. BioNTech Cell & Gene Therapies GmbH reference D7. 11 pages.
Citation in opposition procedure—D12—EP3170842 (opposed patent). Opposition by BioNTech Cell & Gene Therapies GmbH filed Jun. 4, 2020 against EP3170842 Application No. 15821331.4. Consolidated List of Cited Opposition Documents reference D12. BioNTech Cell & Gene Therapies GmbH reference D8. 53 pages.
Citation in opposition procedure—D13—English-language translation of the application as filed PCT/CN2015/084023 (published in Chinese as WO 2016/008405), as filed by the Patentee at the European Patent Office on Jan. 30, 2017. Opposition by BioNTech Cell & Gene Therapies GmbH filed Jun. 4, 2020 against EP3170842 Application No. 15821331.4. Consolidated List of Cited Opposition Documents reference D13. BioNTech Cell & Gene Therapies GmbH reference D8a. 57 pages.
Citation in opposition procedure—D14—CN201410341504. Opposition by BioNTech Cell & Gene Therapies GmbH filed Jun. 4, 2020 against EP3170842 Application No. 15821331.4. Consolidated List of Cited Opposition Documents reference D14. BioNTech Cell & Gene Therapies GmbH reference D9. 51 pages.
Citation in opposition procedure—D15—WO 2016/180782 A1 + sequence listing. Opposition by BioNTech Cell & Gene Therapies GmbH filed Jun. 4, 2020 against EP3170842 Application No. 15821331.4. Consolidated List of Cited Opposition Documents reference D15. BioNTech Cell & Gene Therapies GmbH reference D10. 164 pages.
Citation in opposition procedure—D16—WO 2016/180468 (priority document of D10). Opposition by BioNTech Cell & Gene Therapies GmbH filed Jun. 4, 2020 against EP3170842 Application No. 15821331.4. Consolidated List of Cited Opposition Documents reference D16. BioNTech Cell & Gene Therapies GmbH reference D10a. 160 pages.
Citation in opposition procedure—D17—EP3294333, publication of regional phase of D10. Opposition by BioNTech Cell & Gene Therapies GmbH filed Jun. 4, 2020 against EP3170842 Application No. 15821331.4. Consolidated List of Cited Opposition Documents reference D17. BioNTech Cell & Gene Therapies GmbH reference D10b. 1 page.
Citation in opposition procedure—D18—Annex to D10 showing a sequence alignment between Seq ID No. 6 and Seq ID No. 41 of D10. Opposition by BioNTech Cell & Gene Therapies GmbH filed Jun. 4, 2020 against EP3170842 Application No. 15821331.4. Consolidated List of Cited Opposition Documents reference D18. BioNTech Cell & Gene Therapies GmbH reference D10c. 1 page.
Citation in opposition procedure—D19—Annex to D10 showing the NCBI reference sequence for human CD28. Opposition by BioNTech Cell & Gene Therapies GmbH filed Jun. 4, 2020 against EP3170842 Application No. 15821331.4. Consolidated List of Cited Opposition Documents reference D19. BioNTech Cell & Gene Therapies GmbH reference D10d. 3 pages.
Citation in opposition procedure—D2—Annex to D3 showing a a sequence alignment of Seq ID No. 6 with Seq ID Nos. 2-4 of D3. Opposition by BioNTech Cell & Gene Therapies GmbH filed Jun. 4, 2020 against EP3170842 Application No. 15821331.4. Consolidated List of Cited Opposition Documents reference D2. BioNTech Cell & Gene Therapies GmbH reference D3a. 1 page.
Citation in opposition procedure—D20—Annex to D10 showing the NCBI reference sequence for human CD3£. Opposition by BioNTech Cell & Gene Therapies GmbH filed Jun. 4, 2020 against EP3170842 Application No. 15821331.4. Consolidated List of Cited Opposition Documents reference D20. BioNTech Cell & Gene Therapies GmbH reference D10e. 3 pages.
Citation in opposition procedure—D3—EP3099706, publication of regional phase of D3. Opposition by BioNTech Cell & Gene Therapies GmbH filed Jun. 4, 2020 against EP3170842 Application No. 15821331.4. Consolidated List of Cited Opposition Documents reference D3. BioNTech Cell & Gene Therapies GmbH reference D3b. 1 page.
Citation in opposition procedure—D4—EP2765193 (WO2013/051718). Opposition by BioNTech Cell & Gene Therapies GmbH filed Jun. 4, 2020 against EP3170842 Application No. 15821331.4. Consolidated List of Cited Opposition Documents reference D4. BioNTech Cell & Gene Therapies GmbH reference D4. 62 pages.
Citation in opposition procedure—D5—WO2014/075788A1 + sequence listing. Opposition by BioNTech Cell & Gene Therapies GmbH filed Jun. 4, 2020 against EP3170842 Application No. 15821331.4. Consolidated List of Cited Opposition Documents reference D5. BioNTech Cell & Gene Therapies GmbH reference D5. 349 pages.
Citation in opposition procedure—D6—Annex to D5 showing a sequence alignment of Seq ID No. 6 with Seq ID Nos. 8, 15 and 46 of D5. Opposition by BioNTech Cell & Gene Therapies GmbH filed Jun. 4, 2020 against EP3170842 Application No. 15821331.4. Consolidated List of Cited Opposition Documents reference D6. BioNTech Cell & Gene Therapies GmbH reference D5a. 1 page.
Citation in opposition procedure—D7—Annex to D5 showing a sequence alignment of Seq ID No. 6 with Seq ID No. 38 of D5. Opposition by BioNTech Cell & Gene Therapies GmbH filed Jun. 4, 2020 against EP3170842 Application No. 15821331.4. Consolidated List of Cited Opposition Documents reference D7. BioNTech Cell & Gene Therapies GmbH reference D5b. 1 page.
Citation in opposition procedure—D8—Annex to D5 showing a sequence alignment of Seq ID No. 4 with Seq ID Nos. 6, 11 and 46 of D5. Opposition by BioNTech Cell & Gene Therapies GmbH filed Jun. 4, 2020 against EP3170842 Application No. 15821331.4. Consolidated List of Cited Opposition Documents reference D8. BioNTech Cell & Gene Therapies GmbH reference D5c. 1 page.
Citation in opposition procedure—D9—CN103483453, cited in the ISR as D3. Opposition by BioNTech Cell & Gene Therapies GmbH filed Jun. 4, 2020 against EP3170842 Application No. 15821331.4. Consolidated List of Cited Opposition Documents reference D9. BioNTech Cell & Gene Therapies GmbH reference D6. 58 pages.
Citation in opposition procedure—Exhibit A—Alignment Seq ID_19 with eGFP+SEQID 4. Amino acid sequences contributing to the extracellular binding region of Seq ID No. 19-22. Opposition by BioNTech Cell & Gene Therapies GmbH filed Jun. 4, 2020 against EP3170842 Application No. 15821331.4. 2 pages.
Citation in opposition procedure—Exhibit B—Alignment Seq ID_20 with eGFP+SEQID 4. Amino acid sequences contributing to the extracellular binding region of Seq ID No. 19-22. Opposition by BioNTech Cell & Gene Therapies GmbH filed Jun. 4, 2020 against EP3170842 Application No. 15821331.4. 2 pages.
Citation in opposition procedure—Exhibit C—Alignment Seq ID_21 with eGFP+SEQID 6. Amino acid sequences contributing to the extracellular binding region of Seq ID No. 19-22. Opposition by BioNTech Cell & Gene Therapies GmbH filed Jun. 4, 2020 against EP3170842 Application No. 15821331.4. 2 pages.
Citation in opposition procedure—Exhibit D—Alignment Seq ID_22 with eGFP+SEQID 6. Amino acid sequences contributing to the extracellular binding region of Seq ID No. 19-22. Opposition by BioNTech Cell & Gene Therapies GmbH filed Jun. 4, 2020 against EP3170842 Application No. 15821331.4. 2 pages.
Consolidated list of cited opposition documents. Opposition by BioNTech Cell & Gene Therapies GmbH filed Jun. 4, 2020 against EP3170842 Application No. 15821331.4. Consolidated List of Cited Opposition Documents references D1-D20. 1 page.

(56) References Cited

OTHER PUBLICATIONS

Davies, et al. Combining CD19 redirection and alloanergization to generate tumor-specific human T cells for allogeneic cell therapy of B-cell malignancies. Cancer Res, 2010, 70(10):3915-24.
Extended European Search Report and Search Opinion dated Nov. 29, 2017 for European Patent Application No. 15821331.4.
Grupp, et al., Adoptive cellular therapy, Curr Top Microbiol Immunol., 2011, 344:149-172.
Harmsen et al. Properties, production, and applications of camelid single-domain antibody fragments. Appl. Microbiol. Biotechnol. 77:13-22 (2007).
International search report and written opinion dated Jan. 21, 2016 for PCT/CN2015/084023.
Kim, et al. Enhancement of LFA-1-Mediated T Cell Adhesion by Human T Lymphotropic Virus Type 1 p12. Journal of Immunology, 176(9):5463-70. Year: 2006.
Ma, et al. Current Progress in CAR-T Cell Therapy for Solid Tumors. Int J Biol Sci. 2019; 15(12): 2548-2560. Published online Sep. 7, 2019. doi: 10.7150/ijbs.34213.
Morgan, R.A., et al., Case report of a serious adverse event following the administration of T cells transduced with a chimeric antigen receptor recognizing ERBB2. Molecular Therapy, Apr. 18, 2010. pp. 843-851 vol. 18, No. 4. e-pub Feb. 23, 2010.
Nakazawa, Y. Gene-modified T-cell Therapy Using Chimeric Antigen Receptor. The Shinshu Medical Journal. 2013. vol. 61. Issue 4. pp. 197-203, Released Sep. 25, 2013. https://doi.org/10.11441/shinshumedj.61.197.
Ngo, et al., Ex vivo gene transfer for improved adoptive immunotherapy of cancer Human Molecular Genetics, 2011, 20(1): R93-99.
Notice of allowance dated Apr. 12, 2019 for U.S. Appl. No. 15/326,974.
Notice of Allowance dated Sep. 13, 2021 for U.S. Appl. No. 16/448,053.
Notice of opposition dated Jun. 9, 2020 against EP3170842 Application No. 15821331.4 by BioNTech Cell & Gene Therapies GmbH filed Jun. 4, 2020 with non patent literature (D7) Sadelain at al., "The Basic Principles of Chimeric Antigen Receptor Design" Cancer Discovery, vol. 3, 2013. 44 pages.
Office action dated Jan. 6, 2021 for U.S. Appl. No. 16/448,053.
Office action dated Jan. 30, 2019 for U.S. Appl. No. 15/326,974.
Office action dated Aug. 5, 2021 for U.S. Appl. No. 16/448,053.
Office action dated Sep. 20, 2018 for U.S. Appl. No. 15/326,974.
Sadelain et al. The basic principles of chimeric antigen receptor design. Cancer Discov. 3(4):388-98 (2013).
Sahin, et al. Claudin-18 Splice Variant 2 Is a Pan-Cancer Target Suitable for Therapeutic Antibody Development. Human Cancer Biology. vol. 14. No. 23. pp. 2-13. Dec. 1, 2008.
Stoter, et al., Treatment of metastatic renal cell carcinoma with autologous T-lymphocytes genetically retargeted against carbonic anhydrase IX: first clinical experience, J. Clin. Oncol, 2006, 24(13): e20-e22.
Zhang, et al., Chimeric NKG2D-modified T cells inhibit systemic T-cell lymphoma growth in a manner involving multiple cytokines and cytotoxic pathways, Can Res 2007, 67 (22): 11029-11036.

* cited by examiner

SEQUENCE LISTING

<160> NUMBER OF SEQ ID NOS: 26

<210> SEQ ID NO 1
<211> LENGTH: 727
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleic acid sequence encoding CLD18A2 single
      chain antibody 125

<400> SEQUENCE: 1
gctagcacag gttcagctgc agcagtctgg agctgagctg gcgaggcccg gggcttcagt      60
gaagctgtcc tgcaaggctt ctggctacac cttcactgac tactatataa actgggtgaa     120
gcagaggact ggacagggcc ttgagtggat tggagagatt tatcctggaa gtggtaatac     180
ttactacaat gagaagttca agggcaaggc cacactgact gcagacaaat cctccagcac     240
agcctacatg cagctcagca gcctgacatc tgaggactct gcagtctatt tctgtgcaag     300
atcgtatggt gcctttgact actggggcca aggcaccact ctcacagtct cctcaggtgg     360
aggcggttca ggcggaggtg gctctggcgg tggcggatcg gacattgtga tgacccagtc     420
tcaaaaattc atgtccacat cagtaggaga cagggtcagc atcacctgca aggccagtca     480
gaatgttcgt actgctgtag cctggtatca acagaaacca gggcagtctc ctaaagcact     540
gatttacttg gcatccaacc ggcacactgg agtccctgat cgcttcacag gcagtggatc     600
tgggacagat ttcactctca ccattagcaa tgtgcaatct gaagacctgg cagattattt     660
ctgtctgcaa cattggaatt atcctctgac gttcggtgga ggcaccaagc tggaaatcaa     720
aggatcc                                                              727

<210> SEQ ID NO 2
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of CLD18A2 single chain
      antibody 125

<400> SEQUENCE: 2

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Asp Tyr
            20                  25                  30

Tyr Ile Asn Trp Val Lys Gln Arg Thr Gly Gln Gly Leu Glu Trp Ile
        35                  40                  45

Gly Glu Ile Tyr Pro Gly Ser Gly Asn Thr Tyr Tyr Asn Glu Lys Phe
    50                  55                  60

-continued

```
Lys Gly Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Phe Cys
             85                  90                  95

Ala Arg Ser Tyr Gly Ala Phe Asp Tyr Trp Gly Gln Gly Thr Thr Leu
            100                 105                 110

Thr Val Ser Ser Gly Gly Gly Gly Ser Gly Gly Gly Gly Ser Gly Gly
        115                 120                 125

Gly Gly Ser Asp Ile Val Met Thr Gln Ser Gln Lys Phe Met Ser Thr
130                 135                 140

Ser Val Gly Asp Arg Val Ser Ile Thr Cys Lys Ala Ser Gln Asn Val
145                 150                 155                 160

Arg Thr Ala Val Ala Trp Tyr Gln Gln Lys Pro Gly Gln Ser Pro Lys
                165                 170                 175

Ala Leu Ile Tyr Leu Ala Ser Asn Arg His Thr Gly Val Pro Asp Arg
            180                 185                 190

Phe Thr Gly Ser Gly Ser Gly Thr Asp Phe Thr Leu Thr Ile Ser Asn
        195                 200                 205

Val Gln Ser Glu Asp Leu Ala Asp Tyr Phe Cys Leu Gln His Trp Asn
    210                 215                 220

Tyr Pro Leu Thr Phe Gly Gly Gly Thr Lys Leu Glu Ile Lys
225                 230                 235
```

<210> SEQ ID NO 3
<211> LENGTH: 751
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleic acid sequence encoding CLD18A2 single
      chain antibody 165

<400> SEQUENCE: 3

```
gctagcacag atccagttgg tgcagtctgg acctgagctg aagaagcctg gagagacagt      60
caagatctcc tgcaaggctt ctgggtatac cttcacaaac tatggaatga actgggtgaa     120
gcaggctcca ggaaagggtt taaagtggat gggctggata acaccaaca ctggagagcc      180 aacctatgct gaagagttca aggacggtt tgccttctct ttggaaacct ctgccagcac      240
tgcctatttg cagatcaaca acctcaaaaa tgaggacacg ctacatatt tctgtgcaag      300 actgggtttt ggtaatgcta tggactactg gggtcaagga acctcagtca ccgtctcctc      360
aggtggaggc ggttcaggcg gaggtggctc tggcggtggc ggatcggaca ttgtgatgac      420
acagtctcca tcctcccctga ctgtgacagc aggagagaag gtcactatga gctgcaagtc      480
cagtcagagt ctgttaaaca gtggaaatca aagaactac ttgacctggt accagcagaa      540
accagggcag cctcctaaac tgttgatcta ctgggcatcc actagggaat ctgggtccc      600 tgatcgcttc acaggcagtg gatctggaac agatttcact ctcaccatca gcagtgtgca      660
ggctgaagac ctggcagttt attactgtca gaatgattat agttatccgc tcacgttcgg      720
tgctgggacc aagctggagc tgaaagaatt c                                    751
```

<210> SEQ ID NO 4
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of CLD18A2 single chain
      antibody 163

<400> SEQUENCE: 4

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Leu Gly Phe Gly Asn Ala Met Asp Tyr Trp Gly Gln Gly Thr
            100                 105                 110

Ser Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Ser Ser Leu
    130                 135                 140

Thr Val Thr Ala Gly Glu Lys Val Thr Met Ser Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ala Glu Asp Leu Ala Val
    210                 215                 220

Tyr Tyr Cys Gln Asn Asp Tyr Ser Tyr Pro Leu Thr Phe Gly Ala Gly
225                 230                 235                 240

Thr Lys Leu Glu Leu Lys
                245

<210> SEQ ID NO 5
<211> LENGTH: 751
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleic acid sequence encoding CLD18A2 single
      chain antibody 175

<400> SEQUENCE: 5
gctagcacag gtccaactgc agcagcctgg ggctgagctg gtgaggcctg ggcttcagt      60 gaagctgtcc tgcaaggctt ctggctacac cttcaccagc tactgataaa actgggtgaa    120
gcagaggcct ggacaaggcc ttgagtggat cggaaatatt tatccttctg atagttatac    180
taactacaat caaaagttca aggacaaggc cacattgact gtagacaaat cctccagcac    240

```
agcctacatg cagctcagca gcccgacatc tgaggactct gcggtctatt actgtacaag      300
atcgtggagg ggtaactcct ttgactactg gggccaaggc accactctca cagtctcctc      360
aggtggaggc ggttcaggcg gaggtggctc tggcggtggc ggatcggaca ttgtgatgac      420
acagtctcca tcctccctga ctgtgacagc aggagagaag gtcactatga gctgcaagtc      480
cagtcagagt ctgttaaaca gtggaaatca aaagaactac ttgacctggt accagcagaa      540
accagggcag cctcctaaac tgttgatcta ctgggcatcc actagggaat ctggggtccc      600
tgatcgcttc acaggcagtg gatctggaac agatttcact ctcaccatca gcagtgtgca      660
ggctgaagac ctggcagttt attactgtca gaatgattat agttatccat tcacgttcgg      720 ctcgggggaca aagttggaaa taaaagaatt c                                     751
```

<210> SEQ ID NO 6
<211> LENGTH: 246
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Amino acid sequence of CLD18A2 single chain
antibody 175

<400> SEQUENCE: 6

```
Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser Gly Gly Gly Ser Gly Gly Gly Gly Ser
        115                 120                 125

Gly Gly Gly Gly Ser Asp Ile Val Met Thr Gln Ser Pro Ser Ser Leu
    130                 135                 140

Thr Val Thr Ala Gly Glu Lys Val Thr Met Ser Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ala Glu Asp Leu Ala Val
    210                 215                 220

Tyr Tyr Cys Gln Asn Asp Tyr Ser Tyr Pro Phe Thr Phe Gly Ser Gly
225                 230                 235                 240

Thr Lys Leu Glu Ile Lys
                245
```

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 7
tgctccacgc cgccaggccg cagatccagt tggtgcagtc tg                           42

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 8
cgcggcgctg gcgtcgtggt tttcagctcc agcttggtcc ca                           42

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 9
tgctccacgc cgccaggccg caggtccaac tgcagcagcc                              40

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 10
cgcggcgctg gcgtcgtggt ttttatttcc aactttgtcc ccg                          43

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 11 gcagggggaaa gaatagtaga ca                                                22

<210> SEQ ID NO 12
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 12
cggcctggcg gcgtggagca                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 13
accacgacgc cagcgccgcg                                              20

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 14
tagcgtaaaa ggagcaacat ag                                           22

<210> SEQ ID NO 15
<211> LENGTH: 2183
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleic acid sequence encoding chimeric antigen
      receptor protein CLD18A2-163-Z

<400> SEQUENCE: 15
aagcttacgc gtcctagcgc taccggtcgc caccatggtg agcaagggcg aggagctgtt      60
caccggggtg gtgcccatcc tggtcgagct ggacggcgac gtaaacggcc acaagttcag     120
cgtgtccggc gagggcgagg gcgatgccac ctacggcaag ctgaccctga agttcatctg     180
caccaccggc aagctgcccg tgccctggcc caccctcgtg accaccctga cctacggcgt     240
gcagtgcttc agccgctacc ccgaccacat gaagcagcac gacttcttca agtccgccat     300
gcccgaaggc tacgtccagg agcgcaccat cttcttcaag gacgacggca actacaagac     360
ccgcgccgag gtgaagttcg agggcgacac cctggtgaac cgcatcgagc tgaagggcat     420
cgacttcaag gaggacggca acatcctggg gcacaagctg gagtacaact acaacagcca     480
caacgtctat atcatggccg acaagcagaa gaacggcatc aaggtgaact tcaagatccg     540
ccacaacatc gaggacggca gcgtgcagct cgccgaccac taccagcaga cacccccat     600 cggcgacggc cccgtgctgc tgcccgacaa ccactacctg agcacccagt ccgccctgag     660
caaagacccc aacgagaagc gcgatcacat ggtcctgctg gagttcgtga ccgccgccgg     720
```

```
gatcactctc ggcatggacg agctgtacaa gtccggagtg aaacagactt tgaattttga      780
ccttctgaag ttggcaggag acgttgagtc caaccctggg cccatggcct taccagtgac      840
cgccttgctc ctgccgctgg ccttgctgct ccacgccgcc aggccgcaga tccagttggt      900
gcagtctgga cctgagctga agaagcctgg agagacagtc aagatctcct gcaaggcttc      960
tgggtatacc ttcacaaact atggaatgaa ctgggtgaag caggctccag gaaagggttt     1020
aaagtggatg ggctggataa acaccaacac tggagagcca acctatgctg aagagttcaa     1080
gggacggttt gccttctctt tggaaacctc tgccagcact gcctatttgc agatcaacaa     1140
cctcaaaaat gaggacacgg ctacatattt ctgtgcaaga ctgggttttg gtaatgctat     1200
ggactactgg ggtcaaggaa cctcagtcac cgtctcctca ggtggaggcg gttcaggcgg     1260
aggtggctct ggcggtggcg gatcggacat tgtgatgaca cagtctccat cctcccctga     1320 ctgtgacagca ggagagaagg tcactatgag ctgcaagtcc agtcagagtc tgttaaacag     1380
tggaaatcaa aagaactact tgacctggta ccagcagaaa ccagggcagc tcctaaaact     1440
gttgatctac tgggcatcca ctagggaatc tggggtccct gatcgcttca caggcagtgg     1500
atctggaaca gatttcactc tcaccatcag cagtgtgcag gctgaagacc tggcagttta     1560
ttactgtcag aatgattata gttatccgct cacgttcggt gctgggacca agctggagct     1620
gaaaaccacg acgccagcgc cgcgaccacc aacaccggcg cccaccatcg cgtcgcagcc     1680
cctgtccctg cgcccagagg cgtgccggcc agcggcgggg ggcgcagtgc acacgagggg     1740
gctggacttc gcctgtgata tctacatctg ggcgcccttg gccgggactt gtggggtcct     1800
tctcctgtca ctggttatca ccagagtgaa gttcagcagg agcgcagacg ccccgcgta     1860 ccagcagggc cagaaccagc tctataacga gctcaatcta ggacgaagag aggagtacga     1920
tgttttggac aagagacgtg gccgggaccc tgagatgggg ggaaagccgc agagaaggaa     1980
gaaccctcag gaaggcctgt acaatgaact gcagaaagat aagatggcgg aggcctacag     2040
tgagattggg atgaaaggcg agcgccggag gggcaagggg cacgatggcc tttaccaggg     2100
tctcagtaca gccaccaagg acacctacga cgcccttcac atgcaggccc tgccccctcg     2160
ctaggtcgac ctcgagggaa ttc                                            2183
```

<210> SEQ ID NO 16
<211> LENGTH: 2450
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleic acid sequence encoding chimeric antigen
      receptor protein CLD18A2-163-28BBZ

<400> SEQUENCE: 16

```
aagcttacgc gtcctagcgc taccggtcgc caccatggtg agcaagggcg aggagctgtt       60
caccggggtg gtgcccatcc tggtcgagct ggacggcgac gtaaacggcc acaagttcag      120
cgtgtccggc gagggcgagg gcgatgccac ctacggcaag ctgaccctga agttcatctg      180
caccaccggc aagctgcccg tgccctggcc caccctcgtg accaccctga cctacggcgt      240
gcagtgcttc agccgctacc ccgaccacat gaagcagcac gacttcttca gtccgccat      300 gcccgaaggc tacgtccagg agcgcaccat cttcttcaag gacgacggca actacaagac      360
ccgcgccgag gtgaagttcg agggcgacac cctggtgaac cgcatcgagc tgaagggcat      420
```

```
cgacttcaag gaggacggca acatcctggg gcacaagctg agtacaact acaacagcca      480 caacgtctat atcatggccg acaagcagaa gaacggcatc aaggtgaact tcaagatccg      540
ccacaacatc gaggacggca gcgtgcagct cgccgaccac taccagcaga caccccccat      600
cggcgacggc cccgtgctgc tgcccgacaa ccactacctg agcacccagt ccgccctgag      660
caaagacccc aacgagaagc gcgatcacat ggtcctgctg gagttcgtga ccgccgccgg      720
gatcactctc ggcatggacg agctgtacaa gtccggagtg aaacagactt tgaattttga      780
ccttctgaag ttggcaggag acgttgagtc caaccctggg cccatggcct taccagtgac      840
cgccttgctc ctgccgctgg ccttgctgct ccacgccgcc aggccgcaga tccagttggt      900
gcagtctgga cctgagctga agaagcctgg agagacagtc aagatctcct gcaaggcttc      960
tgggtatacc ttcacaaact atggaatgaa ctgggtgaag caggctccag gaaagggttt     1020
aaagtggatg ggctggataa acaccaacac tggagagcca acctatgctg aagagttcaa     1080
gggacggttt gccttctctt tggaaaacctc tgccagcact gcctatttgc agatcaacaa     1140
cctcaaaaat gaggacacgg ctacatattt ctgtgcaaga ctgggttttg gtaatgctat     1200
ggactactgg ggtcaaggaa cctcagtcac cgtctcctca ggtggaggcg gttcaggcgg     1260
aggtggctct ggcggtggcg gatcggacat tgtgatgaca cagtctccat cctccctgac     1320
tgtgacagca ggagagaagg tcactatgag ctgcaagtcc agtcagagtc tgttaaacag     1380
tggaaatcaa aagaactact tgacctggta ccagcagaaa ccaggcagc ctcctaaact      1440 gttgatctac tgggcatcca ctagggaatc tggggtccct gatcgcttca caggcagtgg     1500
atctggaaca gatttcactc tcaccatcag cagtgtgcag gctgaagacc tggcagttta     1560
ttactgtcag aatgattata gttatccgct cacgttcggt gctgggacca agctggagct     1620
gaaaaccacg acgccagcgc cgcgaccacc aacaccggcg cccaccatcg cgtcgcagcc     1680
cctgtccctg cgcccagagg cgtgccggcc agcggcgggg ggcgcagtgc acacgagggg     1740
gctggacttc gcctgtgatt tttgggtgct ggtggtggtt ggtggagtcc tggcttgcta     1800
tagcttgcta gtaacagtgg cctttattat tttctgggtg aggagtaaga ggagcaggct     1860
cctgcacagt gactacatga acatgactcc ccgccgcccc gggcccaaccc gcaagcatta     1920 ccagccctat gcccccacca cgcgacttcgc agcctatcgc tccaaacggg gcagaaagaa     1980
actcctgtat atattcaaac aaccatttat gagaccagta caaactactc aagaggaaga     2040
tggctgtagc tgccgatttc cagaagaaga agaaggagga tgtgaactga gagtgaagtt     2100
cagcaggagc gcagacgccc ccgcgtacca gcagggccag aaccagctct ataacgagct     2160
caatctagga cgaagagagg agtacgatgt tttggacaag agacgtggcc gggaccctga     2220 gatggggggga aagccgcaga aggaagaa ccctcaggaa ggcctgtaca atgaactgca     2280
gaaagataag atggcggagg cctacagtga gattgggatg aaaggcgagc gccggagggg     2340
caaggggcac gatggccttt accagggtct cagtacagcc accaaggaca cctacgacgc     2400
ccttcacatg caggccctgc cccctcgcta ggtcgacctc gagggaattc                 2450
```

<210> SEQ ID NO 17
<211> LENGTH: 2183
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Nucleic acid sequence encoding chimeric antigen receptor protein CLD18A2-175-Z

<400> SEQUENCE: 17

```
aagcttacgc gtcctagcgc taccggtcgc caccatggtg agcaagggcg aggagctgtt    60
caccggggtg gtgcccatcc tggtcgagct ggacggcgac gtaaacggcc acaagttcag   120
cgtgtccggc gagggcgagg gcgatgccac ctacggcaag ctgaccctga agttcatctg   180
caccaccggc aagctgcccg tgccctggcc caccctcgtg accaccctga cctacggcgt   240
gcagtgcttc agccgctacc ccgaccacat gaagcagcac gacttcttca gtccgccat   300
gcccgaaggc tacgtccagg agcgcaccat cttcttcaag gacgacggca actacaagac   360
ccgcgccgag gtgaagttcg agggcgacac cctggtgaac cgcatcgagc tgaagggcat   420
cgacttcaag gaggacggca acatcctggg gcacaagctg gagtacaact acaacagcca   480
caacgtctat atcatggccg acaagcagaa gaacggcatc aaggtgaact tcaagatccg   540
ccacaacatc gaggacggca gcgtgcagct cgccgaccac taccagcaga caccccat    600
cggcgacggc cccgtgctgc tgcccgacaa ccactacctg agcacccagt ccgccctgag   660
caaagacccc aacgagaagc gcgatcacat ggtcctgctg gagttcgtga ccgccgccgg   720
gatcactctc ggcatggacg agctgtacaa gtccggagtg aaacagactt tgaattttga   780
ccttctgaag ttggcaggag acgttgagtc caaccctggg cccatggcct taccagtgac   840
cgccttgctc ctgccgctgg ccttgctgct ccacgccgcc aggccgcagg tccaactgca   900
gcagcctggg gctgagctgg tgaggcctgg ggcttcagtg aagctgtcct gcaaggcttc   960
tggctacacc ttcaccagct actggataaa ctgggtgaag cagaggcctg acaaggcct  1020
tgagtggatc ggaaatattt atccttctga tagttatact aactacaatc aaaagttcaa  1080
ggacaaggcc acattgactg tagacaaatc ctccagcaca gcctacatgc agctcagcag  1140
cccgacatct gaggactctg cggtctatta ctgtacaaga tcgtggaggg gtaactcctt  1200
tgactactgg ggccaaggca ccactctcac agtctcctca ggtggaggcg ttcaggcgg   1260
aggtggctct ggcggtggcg gatcggacat tgtgatgaca cagtctccat cctccctgac  1320
tgtgacagca ggagagaagg tcactatgag ctgcaagtcc agtcagagtc tgttaaacag  1380
tggaaatcaa aagaactact tgacctggta ccagcagaaa ccaggcagc ctcctaaact   1440
gttgatctac tgggcatcca ctagggaatc tgggtccct gatcgcttca caggcagtgg  1500
atctggaaca gatttcactc tcaccatcag cagtgtgcag gctgaagacc tggcagttta  1560
ttactgtcag aatgattata gttatccatt cacgttcggc tcggggacaa agttggaaat  1620
aaaaaccacg acgccagcgc cgcgaccacc aacaccggcg cccaccatcg cgtcgcagcc  1680
cctgtccctg cgcccagagg cgtgccggcc agcggcgggg ggcgcagtgc acacgagggg  1740
gctggacttc gcctgtgata tctacatctg gcgcccttg ccgggactt gtggggtcct   1800
tctcctgtca ctggttatca ccagagtgaa gttcagcagg agcgcagacg cccccgcgta  1860
ccagcagggc cagaaccagc tctataacga gctcaatcta ggacgaagag aggagtacga  1920
tgttttggac aagagacgtg gccgggaccc tgagatgggg ggaaagccgc agagaaggaa  1980
gaaccctcag gaaggcctgt acaatgaact gcagaaagat aagatggcgg aggcctacag  2040
tgagattggg atgaaaggcg agcgccgag gggcaagggg cacgatggcc tttaccaggg  2100
tctcagtaca gccaccaagg acacctacga cgcccttcac atgcaggccc tgccccctcg  2160
ctaggtcgac ctcgagggaa ttc                                         2183
```

<210> SEQ ID NO 18

<211> LENGTH: 2450
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Nucleic acid sequence encoding chimeric antigen receptor protein CLD18A2-175-28BBZ

<400> SEQUENCE: 18

| | | | | | |
|---|---|---|---|---|---|
| aagcttacgc | gtcctagcgc | taccggtcgc | caccatggtg | agcaagggcg | aggagctgtt | 60 |
| caccggggtg | gtgcccatcc | tggtcgagct | ggacggcgac | gtaaacggcc | acaagttcag | 120 |
| cgtgtccggc | gagggcgagg | gcgatgccac | ctacggcaag | ctgaccctga | agttcatctg | 180 |
| caccaccggc | aagctgcccg | tgccctggcc | caccctcgtg | accaccctga | cctacggcgt | 240 |
| gcagtgcttc | agccgctacc | ccgaccacat | gaagcagcac | gacttcttca | agtccgccat | 300 |
| gcccgaaggc | tacgtccagg | agcgcaccat | cttcttcaag | gacgacggca | actacaagac | 360 |
| ccgcgccgag | gtgaagttcg | agggcgacac | cctggtgaac | cgcatcgagc | tgaagggcat | 420 |
| cgacttcaag | gaggacggca | acatcctggg | gcacaagctg | gagtacaact | acaacagcca | 480 |
| caacgtctat | atcatggccg | acaagcagaa | gaacggcatc | aaggtgaact | tcaagatccg | 540 |
| ccacaacatc | gaggacggca | gcgtgcagct | cgccgaccac | taccagcaga | acacccccat | 600 |
| cggcgacggc | cccgtgctgc | tgcccgacaa | ccactacctg | agcacccagt | ccgccctgag | 660 |
| caaagacccc | aacgagaagc | gcgatcacat | ggtcctgctg | gagttcgtga | ccgccgccgg | 720 |
| gatcactctc | ggcatggacg | agctgtacaa | gtccggagtg | aaacagactt | tgaattttga | 780 |
| ccttctgaag | ttggcaggag | acgttgagtc | caaccctggg | cccatggcct | accagtgac | 840 |
| cgccttgctc | ctgccgctgg | ccttgctgct | ccacgccgcc | aggccgcagg | tccaactgca | 900 |
| gcagcctggg | gctgagctgg | tgaggcctgg | ggcttcagtg | aagctgtcct | gcaaggcttc | 960 |
| tggctacacc | ttcaccagct | actggataaa | ctgggtgaag | cagaggcctg | gacaaggcct | 1020 |
| tgagtggatc | ggaaatattt | atccttctga | tagttatact | aactacaatc | aaaagttcaa | 1080 |
| ggacaaggcc | acattgactg | tagacaaatc | ctccagcaca | gcctacatgc | agctcagcag | 1140 |
| cccgacatct | gaggactctg | cggtctatta | ctgtacaaga | tcgtggaggg | gtaactcctt | 1200 |
| tgactactgg | ggccaaggca | ccactctcac | agtctcctca | ggtggaggcg | gttcaggcgg | 1260 |
| aggtggctct | ggcggtggcg | gatcggacat | tgtgatgaca | cagtctccat | cctccctgac | 1320 |
| tgtgacagca | ggagagaagg | tcactatgag | ctgcaagtcc | agtcagagtc | tgttaaacag | 1380 |
| tggaaatcaa | aagaactact | tgacctggta | ccagcagaaa | ccagggcagc | tcctaaaact | 1440 |
| gttgatctac | tggcatccac | tagggaatc | tggggtccct | gatcgcttca | caggcagtgg | 1500 |
| atctggaaca | gatttcactc | tcaccatcag | cagtgtgcag | gctgaagacc | tggcagttta | 1560 |
| ttactgtcag | aatgattata | gttatccatt | cacgttcggc | tcggggacaa | agttggaaat | 1620 |
| aaaaaccacg | acgccagcgc | cgcgaccacc | aacaccggcg | cccaccatcg | cgtcgcagcc | 1680 |
| cctgtccctg | cgcccagagg | cgtgccggcc | agcggcgggg | ggcgcagtgc | acacgagggg | 1740 |
| gctggacttc | gcctgtgatt | tttgggtgct | ggtggtggtt | ggtggagtcc | tggcttgcta | 1800 |
| tagcttgcta | gtaacagtgg | cctttattat | tttctgggtg | aggagtaaga | ggagcaggct | 1860 |
| cctgcacagt | gactacatga | acatgactcc | ccgccgcccc | gggccaaccc | gcaagcatta | 1920 |
| ccagccctat | gccccaccac | gcgacttcgc | agcctatcgc | tccaaacggg | gcagaaagaa | 1980 |
| actcctgtat | atattcaaac | aaccatttat | gagaccagta | caaactactc | aagaggaaga | 2040 |

```
tggctgtagc tgccgatttc cagaagaaga agaaggagga tgtgaactga gagtgaagtt    2100
cagcaggagc gcagacgccc ccgcgtacca gcagggccag aaccagctct ataacgagct    2160
caatctagga cgaagagagg agtacgatgt tttggacaag agacgtggcc gggaccctga    2220
gatgggggga aagccgcaga gaaggaagaa ccctcaggaa ggcctgtaca atgaactgca    2280
gaaagataag atggcggagg cctacagtga gattgggatg aaaggcgagc gccggagggg    2340 caagggcac gatggccttt accagggtct cagtacagcc accaaggaca cctacgacgc     2400
ccttcacatg caggccctgc cccctcgcta ggtcgacctc gagggaattc                2450

<210> SEQ ID NO 19
<211> LENGTH: 709
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric antigen receptor protein CLD18A2-163-Z

<400> SEQUENCE: 19

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Val Lys Gln Thr Leu Asn Phe Asp Leu Leu Lys Leu Ala Gly Asp
                245                 250                 255

Val Glu Ser Asn Pro Gly Pro Met Ala Leu Pro Val Thr Ala Leu Leu
            260                 265                 270
```

```
Leu Pro Leu Ala Leu Leu Leu His Ala Ala Arg Pro Gln Ile Gln Leu
            275                 280                 285

Val Gln Ser Gly Pro Glu Leu Lys Lys Pro Gly Glu Thr Val Lys Ile
        290                 295                 300

Ser Cys Lys Ala Ser Gly Tyr Thr Phe Thr Asn Tyr Gly Met Asn Trp
305                 310                 315                 320

Val Lys Gln Ala Pro Gly Lys Gly Leu Lys Trp Met Gly Trp Ile Asn
                325                 330                 335

Thr Asn Thr Gly Glu Pro Thr Tyr Ala Glu Phe Lys Gly Arg Phe
                340                 345                 350

Ala Phe Ser Leu Glu Thr Ser Ala Ser Thr Ala Tyr Leu Gln Ile Asn
        355                 360                 365

Asn Leu Lys Asn Glu Asp Thr Ala Thr Tyr Phe Cys Ala Arg Leu Gly
    370                 375                 380

Phe Gly Asn Ala Met Asp Tyr Trp Gly Gln Gly Thr Ser Val Thr Val
385                 390                 395                 400

Ser Ser Gly Gly Gly Gly Ser Gly Gly Gly Gly Ser Gly Gly Gly Gly
                405                 410                 415

Ser Asp Ile Val Met Thr Gln Ser Pro Ser Ser Leu Thr Val Thr Ala
            420                 425                 430

Gly Glu Lys Val Thr Met Ser Cys Lys Ser Ser Gln Ser Leu Leu Asn
        435                 440                 445

Ser Gly Asn Gln Lys Asn Tyr Leu Thr Trp Tyr Gln Gln Lys Pro Gly
    450                 455                 460

Gln Pro Pro Lys Leu Leu Ile Tyr Trp Ala Ser Thr Arg Glu Ser Gly
465                 470                 475                 480

Val Pro Asp Arg Phe Thr Gly Ser Gly Ser Gly Thr Asp Phe Thr Leu
                485                 490                 495

Thr Ile Ser Ser Val Gln Ala Glu Asp Leu Ala Val Tyr Tyr Cys Gln
            500                 505                 510

Asn Asp Tyr Ser Tyr Pro Leu Thr Phe Gly Ala Gly Thr Lys Leu Glu
        515                 520                 525

Leu Lys Thr Thr Thr Pro Ala Pro Arg Pro Pro Thr Pro Ala Pro Thr
    530                 535                 540

Ile Ala Ser Gln Pro Leu Ser Leu Arg Pro Glu Ala Cys Arg Pro Ala
545                 550                 555                 560

Ala Gly Gly Ala Val His Thr Arg Gly Leu Asp Phe Ala Cys Asp Ile
                565                 570                 575

Tyr Ile Trp Ala Pro Leu Ala Gly Thr Cys Gly Val Leu Leu Leu Ser
            580                 585                 590

Leu Val Ile Thr Arg Val Lys Phe Ser Arg Ser Ala Asp Ala Pro Ala
        595                 600                 605

Tyr Gln Gln Gly Gln Asn Gln Leu Tyr Asn Glu Leu Asn Leu Gly Arg
    610                 615                 620

Arg Glu Glu Tyr Asp Val Leu Asp Lys Arg Arg Gly Arg Asp Pro Glu
625                 630                 635                 640

Met Gly Gly Lys Pro Gln Arg Arg Lys Asn Pro Gln Glu Gly Leu Tyr
                645                 650                 655

Asn Glu Leu Gln Lys Asp Lys Met Ala Glu Ala Tyr Ser Glu Ile Gly
            660                 665                 670

Met Lys Gly Glu Arg Arg Arg Gly Lys Gly His Asp Gly Leu Tyr Gln
        675                 680                 685

Gly Leu Ser Thr Ala Thr Lys Asp Thr Tyr Asp Ala Leu His Met Gln
```

```
            690                 695                 700

Ala Leu Pro Pro Arg
705

<210> SEQ ID NO 20
<211> LENGTH: 798
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of chimeric antigen
      receptor protein CLD18A2-163-28BBZ

<400> SEQUENCE: 20

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Val Lys Gln Thr Leu Asn Phe Asp Leu Leu Lys Leu Ala Gly Asp
                245                 250                 255

Val Glu Ser Asn Pro Gly Pro Met Ala Leu Pro Val Thr Ala Leu Leu
            260                 265                 270

Leu Pro Leu Ala Leu Leu Leu His Ala Ala Arg Pro Gln Ile Gln Leu
        275                 280                 285

Val Gln Ser Gly Pro Glu Leu Lys Lys Pro Gly Glu Thr Val Lys Ile
    290                 295                 300

Ser Cys Lys Ala Ser Gly Tyr Thr Phe Thr Asn Tyr Gly Met Asn Trp
305                 310                 315                 320
```

```
Val Lys Gln Ala Pro Gly Lys Gly Leu Lys Trp Met Gly Trp Ile Asn
                325                 330                 335

Thr Asn Thr Gly Glu Pro Thr Tyr Ala Glu Glu Phe Lys Gly Arg Phe
            340                 345                 350

Ala Phe Ser Leu Glu Thr Ser Ala Ser Thr Ala Tyr Leu Gln Ile Asn
            355                 360                 365

Asn Leu Lys Asn Glu Asp Thr Ala Thr Tyr Phe Cys Ala Arg Leu Gly
            370                 375                 380

Phe Gly Asn Ala Met Asp Tyr Trp Gly Gln Gly Thr Ser Val Thr Val
385                 390                 395                 400

Ser Ser Gly Gly Gly Gly Ser Gly Gly Gly Gly Ser Gly Gly Gly Gly
                405                 410                 415

Ser Asp Ile Val Met Thr Gln Ser Pro Ser Ser Leu Thr Val Thr Ala
                420                 425                 430

Gly Glu Lys Val Thr Met Ser Cys Lys Ser Ser Gln Ser Leu Leu Asn
            435                 440                 445

Ser Gly Asn Gln Lys Asn Tyr Leu Thr Trp Tyr Gln Gln Lys Pro Gly
450                 455                 460

Gln Pro Pro Lys Leu Leu Ile Tyr Trp Ala Ser Thr Arg Glu Ser Gly
465                 470                 475                 480

Val Pro Asp Arg Phe Thr Gly Ser Gly Ser Gly Thr Asp Phe Thr Leu
                485                 490                 495

Thr Ile Ser Ser Val Gln Ala Glu Asp Leu Ala Val Tyr Tyr Cys Gln
                500                 505                 510

Asn Asp Tyr Ser Tyr Pro Leu Thr Phe Gly Ala Gly Thr Lys Leu Glu
            515                 520                 525

Leu Lys Thr Thr Thr Pro Ala Pro Arg Pro Pro Thr Pro Ala Pro Thr
            530                 535                 540

Ile Ala Ser Gln Pro Leu Ser Leu Arg Pro Glu Ala Cys Arg Pro Ala
545                 550                 555                 560

Ala Gly Gly Ala Val His Thr Arg Gly Leu Asp Phe Ala Cys Asp Phe
                565                 570                 575

Trp Val Leu Val Val Val Gly Gly Val Leu Ala Cys Tyr Ser Leu Leu
                580                 585                 590

Val Thr Val Ala Phe Ile Ile Phe Trp Val Arg Ser Lys Arg Ser Arg
            595                 600                 605

Leu Leu His Ser Asp Tyr Met Asn Met Thr Pro Arg Arg Pro Gly Pro
            610                 615                 620

Thr Arg Lys His Tyr Gln Pro Tyr Ala Pro Pro Arg Asp Phe Ala Ala
625                 630                 635                 640

Tyr Arg Ser Lys Arg Gly Arg Lys Lys Leu Leu Tyr Ile Phe Lys Gln
                645                 650                 655

Pro Phe Met Arg Pro Val Gln Thr Thr Gln Glu Glu Asp Gly Cys Ser
                660                 665                 670

Cys Arg Phe Pro Glu Glu Glu Glu Gly Gly Cys Glu Leu Arg Val Lys
            675                 680                 685

Phe Ser Arg Ser Ala Asp Ala Pro Ala Tyr Gln Gln Gly Gln Asn Gln
            690                 695                 700

Leu Tyr Asn Glu Leu Asn Leu Gly Arg Arg Glu Glu Tyr Asp Val Leu
705                 710                 715                 720

Asp Lys Arg Arg Gly Arg Asp Pro Glu Met Gly Gly Lys Pro Gln Arg
                725                 730                 735

Arg Lys Asn Pro Gln Glu Gly Leu Tyr Asn Glu Leu Gln Lys Asp Lys
```

```
                        740                 745                 750
Met Ala Glu Ala Tyr Ser Glu Ile Gly Met Lys Gly Glu Arg Arg Arg
                755                 760                 765

Gly Lys Gly His Asp Gly Leu Tyr Gln Gly Leu Ser Thr Ala Thr Lys
            770                 775                 780

Asp Thr Tyr Asp Ala Leu His Met Gln Ala Leu Pro Pro Arg
785                 790                 795

<210> SEQ ID NO 21
<211> LENGTH: 709
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of chimeric antigen
      receptor proteinCLD18A2-175-Z

<400> SEQUENCE: 21

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Val Lys Gln Thr Leu Asn Phe Asp Leu Leu Lys Leu Ala Gly Asp
                245                 250                 255

Val Glu Ser Asn Pro Gly Pro Met Ala Leu Pro Val Thr Ala Leu Leu
            260                 265                 270

Leu Pro Leu Ala Leu Leu Leu His Ala Ala Arg Pro Gln Val Gln Leu
        275                 280                 285
```

```
Gln Gln Pro Gly Ala Glu Leu Val Arg Pro Gly Ala Ser Val Lys Leu
    290                 295                 300

Ser Cys Lys Ala Ser Gly Tyr Thr Phe Thr Ser Tyr Trp Ile Asn Trp
305                 310                 315                 320

Val Lys Gln Arg Pro Gly Gln Gly Leu Glu Trp Ile Gly Asn Ile Tyr
                325                 330                 335

Pro Ser Asp Ser Tyr Thr Asn Tyr Asn Gln Lys Phe Lys Asp Lys Ala
                340                 345                 350

Thr Leu Thr Val Asp Lys Ser Ser Thr Ala Tyr Met Gln Leu Ser
            355                 360                 365

Ser Pro Thr Ser Glu Asp Ser Ala Val Tyr Tyr Cys Thr Arg Ser Trp
    370                 375                 380

Arg Gly Asn Ser Phe Asp Tyr Trp Gly Gln Gly Thr Thr Leu Thr Val
385                 390                 395                 400

Ser Ser Gly Gly Gly Gly Ser Gly Gly Gly Gly Ser Gly Gly Gly Gly
                405                 410                 415

Ser Asp Ile Val Met Thr Gln Ser Pro Ser Ser Leu Thr Val Thr Ala
                420                 425                 430

Gly Glu Lys Val Thr Met Ser Cys Lys Ser Ser Gln Ser Leu Leu Asn
            435                 440                 445

Ser Gly Asn Gln Lys Asn Tyr Leu Thr Trp Tyr Gln Gln Lys Pro Gly
    450                 455                 460

Gln Pro Pro Lys Leu Leu Ile Tyr Trp Ala Ser Thr Arg Glu Ser Gly
465                 470                 475                 480

Val Pro Asp Arg Phe Thr Gly Ser Gly Ser Gly Thr Asp Phe Thr Leu
                485                 490                 495

Thr Ile Ser Ser Val Gln Ala Glu Asp Leu Ala Val Tyr Tyr Cys Gln
            500                 505                 510

Asn Asp Tyr Ser Tyr Pro Phe Thr Phe Gly Ser Gly Thr Lys Leu Glu
    515                 520                 525

Ile Lys Thr Thr Thr Pro Ala Pro Arg Pro Pro Thr Pro Ala Pro Thr
    530                 535                 540

Ile Ala Ser Gln Pro Leu Ser Leu Arg Pro Glu Ala Cys Arg Pro Ala
545                 550                 555                 560

Ala Gly Gly Ala Val His Thr Arg Gly Leu Asp Phe Ala Cys Asp Ile
                565                 570                 575

Tyr Ile Trp Ala Pro Leu Ala Gly Thr Cys Gly Val Leu Leu Leu Ser
            580                 585                 590

Leu Val Ile Thr Arg Val Lys Phe Ser Arg Ser Ala Asp Ala Pro Ala
    595                 600                 605

Tyr Gln Gln Gly Gln Asn Gln Leu Tyr Asn Glu Leu Asn Leu Gly Arg
    610                 615                 620

Arg Glu Glu Tyr Asp Val Leu Asp Lys Arg Arg Gly Arg Asp Pro Glu
625                 630                 635                 640

Met Gly Gly Lys Pro Gln Arg Arg Lys Asn Pro Gln Glu Gly Leu Tyr
                645                 650                 655

Asn Glu Leu Gln Lys Asp Lys Met Ala Glu Ala Tyr Ser Glu Ile Gly
            660                 665                 670

Met Lys Gly Glu Arg Arg Arg Gly Lys Gly His Asp Gly Leu Tyr Gln
    675                 680                 685

Gly Leu Ser Thr Ala Thr Lys Asp Thr Tyr Asp Ala Leu His Met Gln
    690                 695                 700

Ala Leu Pro Pro Arg
```

```
<210> SEQ ID NO 22
<211> LENGTH: 798
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of chimeric antigen
      receptor protein CLD18A2-175-28BBZ

<400> SEQUENCE: 22

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Val Lys Gln Thr Leu Asn Phe Asp Leu Leu Lys Leu Ala Gly Asp
                245                 250                 255

Val Glu Ser Asn Pro Gly Pro Met Ala Leu Pro Val Thr Ala Leu Leu
            260                 265                 270

Leu Pro Leu Ala Leu Leu Leu His Ala Ala Arg Pro Gln Val Gln Leu
        275                 280                 285

Gln Gln Pro Gly Ala Glu Leu Val Arg Pro Gly Ala Ser Val Lys Leu
    290                 295                 300

Ser Cys Lys Ala Ser Gly Tyr Thr Phe Thr Ser Tyr Trp Ile Asn Trp
305                 310                 315                 320

Val Lys Gln Arg Pro Gly Gln Gly Leu Glu Trp Ile Gly Asn Ile Tyr
                325                 330                 335
```

```
Pro Ser Asp Ser Tyr Thr Asn Tyr Asn Gln Lys Phe Lys Asp Lys Ala
            340                 345                 350

Thr Leu Thr Val Asp Lys Ser Ser Thr Ala Tyr Met Gln Leu Ser
        355                 360                 365

Ser Pro Thr Ser Glu Asp Ser Ala Val Tyr Tyr Cys Thr Arg Ser Trp
    370                 375                 380

Arg Gly Asn Ser Phe Asp Tyr Trp Gly Gln Gly Thr Thr Leu Thr Val
385                 390                 395                 400

Ser Ser Gly Gly Gly Ser Gly Gly Gly Ser Gly Gly Gly Gly
                405                 410                 415

Ser Asp Ile Val Met Thr Gln Ser Pro Ser Ser Leu Thr Val Thr Ala
            420                 425                 430

Gly Glu Lys Val Thr Met Ser Cys Lys Ser Ser Gln Ser Leu Leu Asn
            435                 440                 445

Ser Gly Asn Gln Lys Asn Tyr Leu Thr Trp Tyr Gln Gln Lys Pro Gly
        450                 455                 460

Gln Pro Pro Lys Leu Leu Ile Tyr Trp Ala Ser Thr Arg Glu Ser Gly
465                 470                 475                 480

Val Pro Asp Arg Phe Thr Gly Ser Gly Ser Gly Thr Asp Phe Thr Leu
                485                 490                 495

Thr Ile Ser Ser Val Gln Ala Glu Asp Leu Ala Val Tyr Tyr Cys Gln
            500                 505                 510

Asn Asp Tyr Ser Tyr Pro Phe Thr Phe Gly Ser Gly Thr Lys Leu Glu
        515                 520                 525

Ile Lys Thr Thr Thr Pro Ala Pro Arg Pro Pro Thr Pro Ala Pro Thr
    530                 535                 540

Ile Ala Ser Gln Pro Leu Ser Leu Arg Pro Glu Ala Cys Arg Pro Ala
545                 550                 555                 560

Ala Gly Gly Ala Val His Thr Arg Gly Leu Asp Phe Ala Cys Asp Phe
                565                 570                 575

Trp Val Leu Val Val Val Gly Gly Val Leu Ala Cys Tyr Ser Leu Leu
            580                 585                 590

Val Thr Val Ala Phe Ile Ile Phe Trp Val Arg Ser Lys Arg Ser Arg
        595                 600                 605

Leu Leu His Ser Asp Tyr Met Asn Met Thr Pro Arg Arg Pro Gly Pro
    610                 615                 620

Thr Arg Lys His Tyr Gln Pro Tyr Ala Pro Pro Arg Asp Phe Ala Ala
625                 630                 635                 640

Tyr Arg Ser Lys Arg Gly Arg Lys Lys Leu Leu Tyr Ile Phe Lys Gln
                645                 650                 655

Pro Phe Met Arg Pro Val Gln Thr Thr Gln Glu Glu Asp Gly Cys Ser
            660                 665                 670

Cys Arg Phe Pro Glu Glu Glu Glu Gly Gly Cys Glu Leu Arg Val Lys
        675                 680                 685

Phe Ser Arg Ser Ala Asp Ala Pro Ala Tyr Gln Gln Gly Gln Asn Gln
    690                 695                 700

Leu Tyr Asn Glu Leu Asn Leu Gly Arg Arg Glu Glu Tyr Asp Val Leu
705                 710                 715                 720

Asp Lys Arg Arg Gly Arg Asp Pro Glu Met Gly Gly Lys Pro Gln Arg
                725                 730                 735

Arg Lys Asn Pro Gln Glu Gly Leu Tyr Asn Glu Leu Gln Lys Asp Lys
            740                 745                 750

Met Ala Glu Ala Tyr Ser Glu Ile Gly Met Lys Gly Glu Arg Arg Arg
```

Gly Lys Gly His Asp Gly Leu Tyr Gln Gly Leu Ser Thr Ala Thr Lys
755                 760                 765
                770                 775                 780

Asp Thr Tyr Asp Ala Leu His Met Gln Ala Leu Pro Pro Arg
785                 790                 795

<210> SEQ ID NO 23
<211> LENGTH: 1266
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: scFv(GPC3)-CD8-CD3 zeta

<400> SEQUENCE: 23

| | |
|---|---|
| gatgttgtga tgactcagtc tccactctcc ctgcccgtca cccctggaga gccggcctcc | 60 |
| atctcctgca gatctagtca gagccttgta cacagtaatg ccaacaccta tttacattgg | 120 |
| tacctgcaga agccagggca gtctccacag ctcctgatct ataaagtttc caaccgattt | 180 |
| tctggggtcc ctgacaggtt cagtggcagt ggatcaggca cagattttac actgaaaatc | 240 |
| agcagagtgg aggctgagga tgttggggtt tattactgct ctcaaaatac acatgttcct | 300 |
| cctacgtttg ccaggggac caagctggag atcaaacgtg gtggaggcgg ttcaggcgga | 360 |
| ggtggctctg gcggtggcgg atcgcaggtg cagctggtgc agtctggagc tgaggtgaag | 420 |
| aagcctgggg cctcagtgaa ggtctcctgc aaggcttctg gatacacctt caccgactat | 480 |
| gaaatgcact gggtgcgaca ggcccctgga caagggcttg agtggatggg agctcttgat | 540 |
| cctaaaactg gtgatactgc ctacagtcag aagttcaagg gcagagtcac gctgaccgcg | 600 |
| gacgaatcca cgagcacagc ctacatggag ctgagcagc tgagatctga ggacacggcc | 660 |
| gtgtattact gtacaagatt ctactccat acttactggg gccagggaac cctggtcacc | 720 |
| gtctcctcaa ccacgacgcc agcgccgcga ccaccaacac cggcgcccac catcgcgtcg | 780 |
| cagccctgt ccctgcgccc agaggcgtgc cggccagcgg cggggggcgc agtgcacacg | 840 |
| agggggctgg acttcgcctg tgatatctac atctgggcgc ccttggccgg gacttgtggg | 900 |
| gtccttctcc tgtcactggt tatcaccaga gtgaagttca gcaggagcgc agacgccccc | 960 |
| gcgtaccagc agggccagaa ccagctctat aacgagctca atctaggacg aagagaggag | 1020 |
| tacgatgttt tggacaagag acgtggccgg gaccctgaga tggggggaaa gccgcagaga | 1080 |
| aggaagaacc ctcaggaagg cctgtacaat gaactgcaga agataagat ggcggaggcc | 1140 |
| tacagtgaga ttgggatgaa aggcgagcgc cggaggggca aggggcacga tggcctttac | 1200 |
| cagggtctca gtacagccac caaggacacc tacgacgccc ttcacatgca ggccctgccc | 1260 |
| cctcgc | 1266 |

<210> SEQ ID NO 24
<211> LENGTH: 1533
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: scFv(GPC3)-CD28a-CD28b-CD137-CD3 zeta

<400> SEQUENCE: 24

| | |
|---|---|
| gatgttgtga tgactcagtc tccactctcc ctgcccgtca cccctggaga gccggcctcc | 60 |

```
atctcctgca gatctagtca gagccttgta cacagtaatg ccaacaccta tttacattgg    120
tacctgcaga agccagggca gtctccacag ctcctgatct ataaagtttc caaccgattt    180
tctggggtcc ctgacaggtt cagtggcagt ggatcaggca cagattttac actgaaaatc    240
agcagagtgg aggctgagga tgttgggggtt tattactgct ctcaaaatac acatgttcct    300
cctacgtttg ccaggggac caagctggag atcaaacgtg gtggaggcgg ttcaggcgga    360
ggtggctctg gcggtggcgg atcgcaggtg cagctggtgc agtctggagc tgaggtgaag    420
aagcctgggg cctcagtgaa ggtctcctgc aaggcttctg gatacacctt caccgactat    480
gaaatgcact gggtgcgaca ggcccctgga caagggcttg agtggatggg agctcttgat    540
cctaaaactg gtgatactgc ctacagtcag aagttcaagg gcagagtcac gctgaccgcg    600
gacgaatcca cgagcacagc ctacatggag ctgagcagcc tgagatctga ggacacggcc    660
gtgtattact gtacaagatt ctactcctat acttactggg gccagggaac cctggtcacc    720
gtctcctcaa ccacgacgcc agcgccgcga ccaccaacac cggcgcccac catcgcgtcg    780
cagcccctgt ccctgcgccc agaggcgtgc cggccagcgg cggggggcgc agtgcacacg    840 aggggggctgg acttcgcctg tgattttttgg gtgctggtgg tggttggtgg agtcctggct    900
tgctatagct tgctagtaac agtggccttt attattttct gggtgaggag taagaggagc    960
aggctcctgc acagtgacta catgaacatg actccccgcc gccccgggcc aacccgcaag   1020
cattaccagc cctatgcccc accacgcgac ttcgcagcct atcgctccaa cggggcaga   1080 aagaaactcc tgtatatatt caaacaacca tttatgagac cagtacaaac tactcaagag   1140
gaagatggct gtagctgccg atttccagaa gaagaagaag aggatgtga actgagagtg   1200 aagttcagca ggagcgcaga cgcccccgcg taccagcagg gccagaacca gctctataac   1260
gagctcaatc taggacgaag agaggagtac gatgttttgg acaagagacg tggccgggac   1320
cctgagatgg ggggaaagcc gcagagaagg aagaaccctc aggaaggcct gtacaatgaa   1380
ctgcagaaag ataagatggc ggaggcctac agtgagattg gatgaaaagg cgagcgccgg   1440
aggggcaagg ggcacgatgg cctttaccag ggtctcagta cagccaccaa ggacacctac   1500
gacgcccttc acatgcaggc cctgccccct cgc                                1533
```

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Tyr Lys Asp Asp Asp Lys
1               5

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Gly Gly Gly Ser Gly Gly Gly Gly Ser Gly Gly Gly Gly Ser
1               5                   10                  15

IMMUNOLOGIC EFFECTOR CELL OF TARGETED CLD18A2, AND PREPARATION METHOD AND USE THEREOF

CROSS REFERENCE

This application is a continuation application of U.S. patent application Ser. No. 16/448,053, filed Jun. 21, 2019, now U.S. Pat. No. 11,198,729, which is a continuation application of U.S. patent application Ser. No. 15/326,974, filed Jan. 17, 2017, now U.S. Pat. No. 10,377,822, which is a national stage entry of International Application No. PCT/CN2015/084023, filed Jul. 15, 2015, which claims priority to Chinese Patent Application No. 201410341504.X, filed Jul. 17, 2014, each of which is entirely incorporated herein by reference.

SEQUENCE LISTING

The instant application contains a Sequence Listing which has been submitted electronically in ASCII format and is hereby incorporated by reference in its entirety. Said ASCII copy, created on Jun. 8, 2022, is named 60616-703_302_SL.txt and is 57,632 bytes in size.

TECHNICAL FIELD

The invention belongs to the field of cell therapy for tumor, and particularly relates to an immune effector cell targeting CLD18A2, a preparation method and application thereof.

TECHNICAL BACKGROUND

Attention has been increasingly paid to the role of T lymphocytes in tumor immune responses. The Adoptive immunotherapy based on T lymphocytes has a certain effect in some tumors, moreover, such immune therapy method can overcome the above defects of antibody treatment, however, the therapeutical effect in most tumors is still not satisfactory [Grupp S A, et al. Adoptive cellular therapy. Curr Top Microbiol Immunol., 2011; 344:149-72]. In recent years, based on the discovery that the identification of a target Cell by CTL is specifically dependent on a T lymphocyte receptor (T Cell receptor, TCR), the scFv of the antibody against tumor cell-related antigen is fused to intracellular signal activation motif such as T-lymphocyte receptor CD3ζ or FcεRIγ to form Chimeric antigen receptors (CAR), and can be genetically modified on the surface of T lymphocyte by means such as lentivirus infection. Such CAR T lymphocyte can selectively direct T lymphocyte to tumor cells and specifically kill tumor cells in a major histocompatibility complex (MHC)-independent manner. CAR T lymphocytes are new immune therapy strategy in the tumor immunotherapy field [Schmitz M, et al. Chimeric antigen receptor-engineered T cells for immunotherapy of Cancer. J Biomed Biotechnol, 2010, doi:10.1155/2010/956304].

Chimeric antigen receptor comprises an extracellular binding domain, a transmembrane region and an intracellular signaling domain. Generally, the extracellular domain comprises an scFv that is capable of recognizing a tumor-associated antigen, the transmembrane region employs the transmembrane region from molecules such as CD8, CD28 and the likes, and the intracellular signaling domain employs an immunoreceptor tyrosine-based activation motif (ITAM) CD3ζ or FcεRIγ and the intracellular signaling domain of co-stimulatory signaling molecule such as CD28, CD27, CD137, CD134 and the likes.

In the first generation CAR T lymphocyte, the intracellular signaling domain comprises ITAM only, and parts of the chimeric antigen receptor are connected in the form of scFv-TM-ITAM. Such CAR T can induce cellular cytotoxic effect against tumor, but the level of cytokines secreted is relatively low, and no sustaining anti-tumor effect could be induced in the body (Zhang T. et al., Chimeric NKG2D-modified T cells inhibit systemic T-cell lymphoma growth in a manner involving multiple cytokines and cytotoxic pathways, Can Res 2007, 67 (22): 11029-11036).

In the second generation CAR T lymphocyte that developed afterwards, an intracellular signaling domain of CD28 or CD 137 (also known as 4-1BB) is further included, and parts of the chimeric antigen receptor are connected in the form of scFv-TM-CD28-ITAM or scFv-TM-/CD137-ITAM. Co-stimulatory effect of B7/CD28 or 4-1BBL/CD137 in the intracellular signaling domain induces sustained proliferation of T lymphocytes, and is capable of increasing the level of cytokines such as IL-2, IFN-γ and others secreted by T lymphocytes, as well as improving the in vivo survival period and the anti-tumor effect of the CAR T (Dotti G. et al., CD28 costimulation improves expansion and persistence of chimeric antigen receptor modified T cells in lymphoma patients. J Clin Invest, 2011, 121 (5):1822-1826).

In the third generation CAR T lymphocyte that developed in recent years, parts of the chimeric antigen receptor are connected in the form of scFv-TM-CD28-CD137-ITAM or scFv-TM-CD28-CD134-ITAM, the in vivo survival and the anti-tumor effect of the CAR T is further improved (Carpenito C, et al., Control of large established tumor xenografts with genetically retargeted human T cells containing CD28 and CD 137 domains, PNAS, 2009, 106(9): 3360-3365).

Besides the attractive prospect of CAR T lymphocyte in tumor immunotherapy, its relatively high risk shall be taken into account. For instance, certain normal tissue(s) may exhibit low expression of specific antigen to be recognized by the CAR, this may results in damage by CAR T lymphocytes to such normal tissues. For example, treatment against carbonic anhydrase IX (CAIX), the antigen expressed in tumor cells of patients having renal cell carcinoma, is the first reported case of clinical application of adoptive therapy with CAR T lymphocytes, which is also the first case reporting on-target off-tumor effect of CAR T lymphocytes. After multiple administrations of CAR T lymphocytes, patients developed liver toxicity of grades 2-4. Upon analysis, the cause is believed to be the CAIX expression in a low level on bile duct epithelial cells, this clinical trial was discontinued while assessment about therapeutic outcomes in patients are excluded (Stoter G. et al., Treatment of metastatic renal cell carcinoma with autologous T-lymphocytes genetically retargeted against carbonic anhydrase IX: first clinical experience, J clin oncol, 2006, 24 (13): e20-e22; Ngo M C, et al., Ex vivo gene transfer for improved adoptive immunotherapy of cancer Human Molecular Genetics, 2011, R1_R7). Furthermore, the excessive co-stimulation signal in CAR may reduce the threshold required for activating effector cells, such that genetically modified T lymphocyte may be activated at conditions of rather low level of antigen or at the absence of antigen pulse, and resulting in the release of large amount of cytokines which may induce so-called "cytokine storm". This signal leakage will cause off-target cytotoxicity, resulting in non-specific tissue damage. For example, sudden death of a patient caused by such "cytokine storm" induced by low Her2 expression in normal lung tissue was observed during a clinical treatment using a third-generation CAR T cells targeting Her2 for patients having advanced colorectal cancer with liver and lung metastasis (Morgan R A, et al., Report of a serious adverse event following the administration of T cells transduced with a chimeric antigen receptor recognizing Erbb2 Molecular Therapy, 2010, 18 (4): 843-851).

When CAR T is designed, selection of the antigen gene target is crucial. Because of the complexity of in-vivo gene expression and various uncontrollable factors, it is extremely difficult to select a suitable gene for CAR T. Furthermore, for many tumor-specific antigens, it is very difficult to find specific molecule directing at it and suitable to construct CAR-modified immune effector cell. After the CAR T is established, it is often unable to obtain an active extracellular binding region, which is also a difficulty for developing CAR T technology.

SUMMARY OF THE INVENTION

The object of the present invention is to provide an immune effector cell targeting CLD18A2 and the preparation method and use thereof.

In a first aspect of the present invention, it is provided chimeric antigen receptor (CAR) expressed on the surface of an immune effector cell, wherein the chimeric antigen receptor comprises sequentially connected extracellular binding region, transmembrane region and intracellular signal region, wherein the extracellular binding region comprises protein which specifically recognizes CLD18A2 (claudin18.2).

In one preferred embodiment, the protein specifically recognizing CLD18A2 is an antibody or a ligand; preferably, the antibody is a single-chain antibody or a domain antibody.

In another preferred embodiment, the transmembrane region is a sequence comprising transmembrane regions and hinge regions of CD8 or CD28.

In another preferred embodiment, the intracellular signal region is selected from the intracellular signal region sequence of the following: CD3ζ, FcεRIγ, CD27, CD28, CD137, and CD134, and a combination thereof.

In another preferred embodiment, the chimeric antigen receptor comprises an extracellular binding region, a transmembrane region and an intracellular signal region connected in the following sequence:

Single chain antibody specifically recognizing the CLD18A2, CD8 and CD3ζ;

Single chain antibody specifically recognizing CLD18A2, CD8, CD137 and CD3ζ;

Single chain antibody specifically recognizing CLD18A2, transmembrane region of CD28(CD28a), intracellular signal region of CD28 molecule (CD28b) and CD3ζ; or Single chain antibody specifically recognizing CLD18A2, transmembrane region of CD28, intracellular signal region of CD28, CD137 and CD3ζ.

In another preferred embodiment, the chimeric antigen receptor comprises any one of the amino acid sequence of SEQ ID NO: 19-22.

In another preferred embodiment, the immune effector cell comprises T lymphocytes, NK cells or NKT cells.

In another aspect of the invention, it is provided the nucleic acid encoding the chimeric antigen receptor.

In one preferred embodiment, the nucleic acid comprises any one of the nucleotide sequence of SEQ ID NO: 15-18.

In another aspect of the present invention, it is provided an expression vector comprising the aforementioned nucleic acid.

In one preferred embodiment, the expression vector is derived from lentivirus plasmid PWPT (or PWPT-eGFP).

In another aspect of the present invention, it is provided a virus, wherein the said virus (such as lentiviral vector) comprising said vector.

In another aspect of the invention, it is provided the use of the chimeric antigen receptor, the nucleic acid, the expression vector, or the virus, for preparing a genetically modified immune effector cell targeting CLD18A2.

In another aspect of the invention, it is provided a genetically modified immune effector cell transducted by said nucleic acid, said expression vector, or said virus.

In another aspect of the invention, it is provided a genetically modified immune effector cell wherein a chimeric antigen receptor is expressed on the surface thereof, wherein the amino acid sequence of the chimeric antigen receptor is selected from any one of the amino acid sequences of SEQ ID NOs: 19-22.

In another aspect of the present invention, it is provided the use of the genetically modified immune effector cells for preparation of a medicine for suppressing tumor, wherein the tumor is CLD18A2 positive (high-expression) tumor.

In another preferred embodiment, the CLD18A2 positive tumor includes pancreatic cancer, gastric cancer.

Other aspects of the invention will be apparent to those skilled in the art from the disclosure herein.

DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF THE PREFERRED EMBODIMENTS

Figure 1:
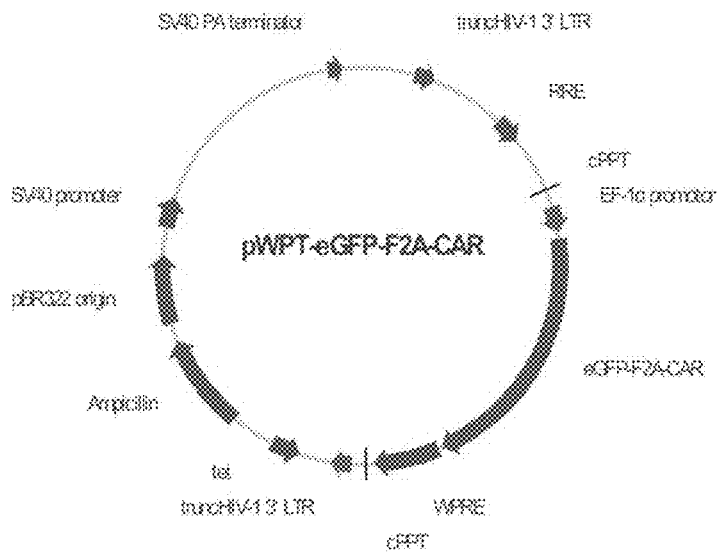
FIG. 1 is the structure schematic diagram of the present lentivirus vector pWPT-eGFP-F2A-CAR comprising CAR coding sequence.

Through thorough and in-depth study, the inventors discloses for the first time a CAR modified immune effector cell based on CLD18A2 gene and the preparation method thereof.

CLD18A2 Gene

At early stage, the inventors investigated various kinds of tumor-specific genes and found that a relatively large part of these genes are also expressed in part of normal tissue cells, thus unable to be applied in the chimeric antigen receptor T cell. Some tumor-specific genes have better tumor-specific expression characteristics, but the CAR-modified immune effector cells correspondingly designed do not have or have rather low tumor cytotoxicity. This may be caused by that the proteins expressed by corresponding genes have low antigenicity, or expressed on an inapposite location, or expressed at a level not high enough, etc. It is also possibly caused by the recombinant construction process which weakened the tumor killing ability of T lymphocytes or cause the tumor killing ability lost.

After repeated investigation and screening, the inventors discovered CLD18A2 gene as the target gene for designing CAR modified immune effector cell (for example, T lymphocyte). Claudin 18 (CLD18) molecule (Genbank accession number: splice variant 1 (CLD18A1): NP.sub.-057453, NM.sub.-016369, and splice variant 2 (CLD18A2): NM.sub.-001002026, NP.sub.-001002026) is a transmembrane protein with a molecular weight of about 27.9/27.72 kD. Claudins is a tightly-connected membrane protein which locates on the epithelium and the endothelium.

Study shows that the CLD18A1 selectively expresses on the normal lung and stomach epithelium, while the CLD18A2 only expresses on differentiated cells with short lifespan in stomach epithelium, not on gastric stem cells. Meanwhile, researches have indicated that the CLD18A2 is expressed on various tumor cells. In view of the above-described characteristics of CLD18A2, the inventors have speculated CLD18A2 be an important therapeutic target for these tumors. Said speculation has been verified by abundant subsequent work.

Chimeric Antigen Receptor and the Coding Nucleic Acid Thereof

The present invention provides a chimeric antigen receptor expressed on the surface of T lymphocyte, wherein the chimeric antigen receptor comprises sequentially connected extracellular binding region, transmembrane region and intracellular signal region, wherein the extracellular binding region comprises protein that specifically recognizes CLD18A2 (claudin 18.2). The chimeric antigen receptor is expressed on the surface of T lymphocyte, which make the T lymphocyte has highly specific cytotoxic effect on tumor cells which expressed CLD18A2 at a high level.

As a preferred mode of the present invention, the extracellular binding region comprises a single-chain antibody scFv that specifically recognizes CLD18A2 The extracellular binding region of the abovementioned chimeric antigen receptor protein is connected with a transmembrane region of CD8 or CD28 through a CD8 hinge region, and the cross-membrane region is immediately followed by the intracellular signal region.

The present invention also includes nucleic acid encoding the chimeric antigen receptors. The nucleic acid sequence of the present invention can be a DNA form or a RNA form. The DNA form comprises cDNA, genomic DNA, or artificially synthesized DNA. DNA can be single-stranded or double-stranded, a coding chain or a non-coding chain. The codons of the nucleic acid of the present invention coding the amino acid sequence of the present chimeric antigen receptor protein can be degenerate, that is, a variety of degenerate nucleic acid sequences encoding the same amino acid sequence are included in the scope of the present invention. The degenerate nucleic acid codons encoding corresponding amino acid are well known in the art. The present invention also relates to variants of the polynucleotide, which encode polypeptides or fragments, analogs and derivatives of the polypeptides having the same amino acid sequences as the present invention. The variants of the polynucleotide can be naturally occurring allelic variants or non-naturally occurring variants. These nucleotide variants include substitution variants, deletion variants, and insertion variants. As is known in the art, an allelic variant is an alternative form of a polynucleotide, which may be substitution, deletion or insertion of one or more nucleotides, but does not substantially alter the functionality of the polypeptide coded thereby.

The monoclonal antibody specifically recognizing human CLD18A2 can be chosen from the the antibodies disclosed in the prior art. A variety of monoclonal antibodies that recognize the c-terminal epitope of CLD18A2 may be applied in the present invention in a suitable manner, as long as after the recombinant construction, CAR-modified immune effector cell with killing activity can finally be obtained. Preferably, a single-chain antibody, more preferably the single-chain antibodies are 163 and 175 antibodies; The 163 and 175 antibodies can specifically recognize CLD18A2 but not CLD18A1. More preferably, they are connected to Fc (ScFv-163 and ScFv-175).

The term "single-chain antibody (scFv) fragment" as used herein refers to an antibody fragment defined as follows. It is a recombinant protein comprising heavy chain variable region (VH) and a light chain variable region (VL) connected by a linker, and the linker associates the two domains by which an antigen binding site is finally formed. The size of the scFv is generally ⅙ of one complete antibody. Preferably, single-chain antibody is one amino acid chain sequence coded by one nucleotide chain. Single-chain antibodies used in the present invention may be used alone or in combination with conventional techniques known in the art, for example, amino acid deletion, insertion, substitution, addition, and/or recombination and/or other modification methods for further modification. It is well known to those skilled in the art to introduce modification in the DNA sequence according to the amino acid sequence of the antibody, for example, see Sambrook, Molecular Cloning: A laboratory Manual, Cold Spring Harbor Laboratory (1989) N.Y. The modification is preferably performed on the nucleic acid level. The above single-chain antibodies can also comprise derivatives thereof. The "derivatives of antibodies" in the present invention include, for example, derivatives of the antibodies which obtained by phage display techniques, and the binding efficiency of said antibodies with CLD18A2 antigen epitope is increased by surface plasmon resonance technique that used in the Biacore system (Schier, Human Antibodies Hybridomas 7 (1996), 97-105; Malmborg «*Journal of Immunological Methods*», 1995, 183:7-13). Also included are those antibody derivatives produced by the preparation method of chimeric antibody described in for example WO89/09622, the humanized antibody preparation method described in EP-A10239400 and WO90/07861, the method for producing xenogeneic antibodies, for example human antibodies in mice, which is mentioned in WO 91/10741, WO 94/02602, and WO 96/33735.

The term "specific recognition" of the present invention means that the antibody of the present invention does not react with or substantially does not react with any polypeptide other than a target antigen. The degree of specificity can be determined by immunology techniques including, but not limited to, immunoblotting, immunoaffinity chromatography, flow cytometry and the like. In the present invention, the specific recognition is preferably determined by flow cytometry. Under particular conditions, the standard of specific recognition can be determined by those of ordinary skill in the art based on their knowledge of the art.

The transmembrane region of the chimeric antigen receptor can be selected from the transmembrane region of proteins such as CD8 or CD28. CD8 or CD28 are the natural markers on the surface of T lymphocyte. Human CD8 protein is a heterodimer, consisted of two chains, αβ or γδ. In one embodiment of the invention, the transmembrane region is selected from the transmembrane region of CD8 alpha or CD28. Additionally, the CD8 alpha hinge region (hinge)) is a flexible region. Therefore, the transmembrane region of CD8 or CD28 and the hinge region can be used to connect the target recognition domain scFv with an intracellular signal region in the chimeric antigen receptor (CAR).

The intracellular signal region may be selected from the intracellular signal regions of CD3ζ, FcεRIγ, CD28, CD137 and CD134 proteins, and combinations thereof. The CD3 molecule consists of five subunits, wherein CD3 subunit (also called as CD3 zeta, for short "Z")) comprises a 3-ITAM motif, which is an important signal transduction region in TCR-CD3 complex. CD3δZ is a truncated CD3ζ sequence without ITAM motif, which is commonly used for constructing negative control in the practice of the present invention. FcεRIγ is mainly distributed on both mast cells and basophilic granulocyte surfaces, which contains an ITAM motif, and is similar to CD3ζ in structure, distribution and function. Furthermore, as previously described, CD28, CD137 and CD134 are co-stimulating signal molecules, which can cause sustained proliferation of T lymphocytes by the co-stimulation action generated by the intracellular signal segments after binding with the respective ligands, and can increase the level of cytokines secreted by T lymphocyte such as IL-2 and the IFN-gamma and the like, while increasing the survival cycle in vivo and the anti-tumor effect of the CAR-modified immune effector cells.

The anti-CLD18A2 chimeric antigen receptor protein coded by the nucleic acid of the present invention can be sequentially connected according to the following manner:
scFv(CLD18A2)-CD8-CD3ζ,
scFv(CLD18A2)-CD8-CD137-CD3ζ,
scFv(CLD18A2)-CD28a-CD28b-CD3ζ,
scFv(CLD18A2)-CD28a-CD28b-CD137-CD3ζ
and combinations thereof, wherein CD28a in the related chimeric antigen receptor protein represents a CD28 transmembrane region, CD28b represents intracellular signal region of CD28 molecules. The various anti-CLD18A2 chimeric antigen receptors above are collectively referred to as scFv (CLD18A2)-CAR.

In one embodiment of the invention, the nucleic acid disclosed by the invention has the sequence as shown in SEQ ID NO: 15-18. In another embodiment of the present invention, the nucleic acid of the present invention is a nucleic acid encoding the chimeric antigen receptor protein as shown in one of SEQ ID NOs: 19-22.

Expression Vector and Cell

The present invention also provides vector comprising the nucleic acid encoding the abovementioned chimeric antigen receptor protein expressed on the surface of T lymphocyte. In one embodiment, the vector used in the present invention is a lentivirus plasmid vector pWPT-eGFP. Said plasmid belongs to a third-generation self-inactivated lentivirus vector system, which have 3 plasmids, that is, the packing plasmid psPAX2 encoding protein Gag/Pol and Rev protein; envelope vector PMD2.G encoding VSV-G protein; and empty vector PWPT-eGFP, which can be used for recombinant introduction of the target nucleic acid sequence, that is, a nucleic acid sequence encoding a CAR. In the empty vector pWPT-eGFP (which itself is mock in the following experiments), the elongation factor-1 alpha (EF-1α) promoter regulates the expression of the enhanced green fluorescent protein (eGFP), while in the recombinant expression vector encoding target gene CAR, the co-expression of eGFP and CAR is realized via ribosome skipping sequence 2A (shortened as "F2A") from food-and-mouth disease virus (FMDV).

The present invention further comprises the virus comprising such plasmid. The virus disclosed by the invention comprises infectious virus after packing, as well as the to-be-packaged virus comprising essential element for packaging into an infectious virus. Other viruses known in the art for transferring foreign genes into T lymphocytes and their corresponding plasmid vectors can also be used in the present invention.

In one embodiment of the invention, the said virus is a lentivirus comprising the above-mentioned pWPT-eGFP-F2A-CAR recombinant vector (namely, comprising scFv (CLD18A2)-CAR).

The invention also provides a genetically modified T lymphocyte, which is transducted by the present nucleic acid, the present recombinant plasmid comprising the above mentioned nucleic acid, or the virus comprising the said plasmid. Conventional nucleic acid transduction methods in the present field, including non-viral and viral transduction methods, can be used in the present invention. The non-virus-based transduction method comprises electroporation method and transposition method. Recently, Nucleofector nuclear transfection apparatus developed by Amaxa can directly introduce foreign gene into the nucleus to realize high-efficiency transduction of target gene. In addition, the transduction efficiency of the transposon systems based on Sleeping Beauty system or PiggyBac transposon is greatly improved compared with that of common electroporation method, and it has already been reported about the combinative application of Nucleofector transfection apparatus and the Sleeping Beauty system (Davies J K., et al. Combining CD19 redirection and alloanergization to generate tumor-specific human T cells for allogeneic cell therapy of B-cell malignancies. Cancer Res, 2010, 70(10): OF1-10.) Such method not only has relatively high transduction efficiency but also can achieve site-directed integration of target genes. In one embodiment of the invention, the T lymphocyte transduction method for realizing the modification of the chimeric antigen receptor is based on virus such as retrovirus or lentivirus. The said method has advantages such as high transduction efficiency, stable expression of foreign genes, and can shorten the time for in-vitro culture of T lymphocytes to reach clinical scale. The transducted nucleic acid is expressed on the surface of the transgenetic T lymphocyte through transcription and translation. In vitro cytotoxity assay on various differently cultured tumor cells prove that the T lymphocyte modified by the present anti-CLD18A2 chimeric antigen receptor gene has highly specific tumor cell killing effect (also known as cytotoxicity). Therefore, the present nucleic acid encoding the chimeric antigen receptor protein, the plasmid comprising the said nucleic acid, the virus comprising the said plasmid and the transgenic T lymphocytes transducted by the above nucleic acids, plasmids or virus can be effectively used for tumor immunotherapy.

In one embodiment, the genetically modified T lymphocyte of the invention expresses a chimeric antigen receptor on the surface thereof, wherein the chimeric antigen receptor is coded and expressed by a nucleic acid of one of SEQ ID NOs: 15-18. In another embodiment, the transgenic T lymphocyte surface of the present invention expresses a chimeric antigen receptor, whose amino acid sequence is selected from one of SEQ ID NOs: 19-22.

Since currently there is no report of the CAR T targeting CLD18A2, the inventors for the first time successfully discovered an immune effector cell (eg, T lymphocyte) suitable for CAR modification from numerous tumor related genes, and successfully prepared CAR-modified immune effector cells. Thus, a brand new treatment means is provided for tumors such as pancreatic cancer and stomach cancer.

The embodiments of the present invention are further described below with reference to specific examples. It should be understood that these embodiments are for illustrative purposes only and are not intended to limit the scope of the invention. The experimental methods not specially noted of particular conditions are usually according to conventional conditions, such as those described in J. Sambrook et. al., Eds, Molecular Cloning: A laboratory Manual, 3'rd edition, Science Publishing House (2002), or the conditions recommended by the manufacturer.

Example 1 the Expression of Single-Chain Antibody Against CLD18A2

By repeatedly researching and analyzing, the inventors identified several scFv antibodies recognizing CLD18A2, for short, referred as 125,163, and 175.

125 (SEQ ID NO: 1 (nucleotide), 2 (amino acid)), 163 (SEQ ID NO: 3 (nucleotide), 4 (amino acid)), 175 (SEQ ID NO: 5 (nucleotide), and 6 (amino acid)) single-chain antibody sequences were synthesized by genetic synthesis based on bridging PCR. The synthesized products were digested by Nhe1/BamH1 (purchased from NEB), ligated in plasmid vector pCMV-V5-Fc (the said plasmid fuses and expresses human antibody Fc at the downstream of the multi-cloning site, hereinafter referred to as V5-Fc for short, purchased from Shanghai raygene biotechnology Co., LTD) digested by the same Nhe1/BamH1 via T4 DNA and was transformed into the host bacterium TOP10. The clones were picked and positive clones were identified by PCR, and confirmed by sequencing. V5-scFv-125-Fc, V5-scFv-163-Fc, and V5-scFv-175-Fc eukaryotic expression plasmid were obtained.

Figure 3:
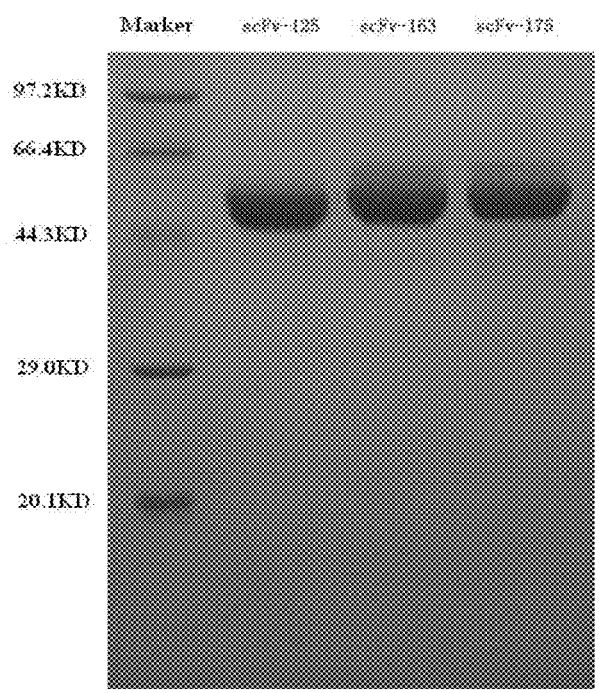
FIG. 3 is the electrophoresis image of the purified anti-CLD18A2 single chain antibody of Example 1.

The above expression plasmids were used to transfect well grown HEK-293F, cultured at 37° C., 5% CO$_2$, 125 rpm on a shaking bed for 7 days. They were centrifuged for 10 min at 4000 rpm, and precipitate was removed. The supernatant were collected and filtered with a 0.45 μm filter film. The processed sample was purified by protein A affinity column (purchased from GE), and eventually the purified single-chain antibody-Fc fusion protein scFv-125-fc (for short scFv-125), scFv-163-fc (scFv-163 for short), scFv-175-fc (scFv-175 for short) were obtained. The identification result is shown in FIG. 3.

Example 2. Construction of the Stable Expression Cell Line of CLD18A1 or CLD18A2

1. Construction of Expression Vectors of CLD18A1 and CLD18A2 and Preparation of Lentivirus The complete coding sequences of CLD18A1 (GenBank: NM_016369) and CLD18A1 complete coding sequence (Genbank: nm_001002026) were synthesized by genetic synthesis technology based on bridging PCR. A flag tag (DYKDDDK (SEQ ID NO: 25)) was inserted into the c-terminal, and MluI/SalI (purchased from NEB) were added at both ends of the synthesized gene segments. The segments were double-digested by MluI/SalI, ligated in plasmid vector pWPT (purchased from addgene) double-digested by the same MluI/SalI via T4 DNA, and were transformed into the host bacterium TOP10. The clones were picked and identified by PCR, and confirmed by sequencing. That correct lentivirus vector plasmid PWPT-CLD18A1, PWPT-CLD18A2 were obtained. The above plasmids and packing accessory plasmids (pGag-pol, pREV, pVsv-g (all purchased from addgene)) were co-transfected at a certain ratio to 293T cell. After 48 h and 72 h of transfection, CLD18A1 and CLd18A2 virus solutions were collected, sub-packed, and stored at −80° C.

2. Establishment of Stable Exogenous Expression Lineage for CLD18A1 and CLD18A2 and Western Blot Assay The above collected CLD18A1 or CLD18A2 virus solutions were added into 293T cells in 6 cm dish respectively. After 72 hours, cells were collected and were lysed by cell lysis solution. On the other hand, human stomach cancer BGC-823 (purchased from Shanghai cell library of Institution of Science of China, TCHu11) and NCI-N87 (purchased from ATCC, CRL-5822) were infected by CLD18A2 virus, respectively. After the cells grew to full, they were lysed by cell lysis solution. 40 μg protein from collected lysed cells were subjected to SDS-PAGE gel electrophoresis, and the gel was assayed by immunoblotting, stained with mouse anti-FLAG antibody (purchased from sigma Aldrich). After PBS wash, incubated together with goat anti-mouse antibodies labeled by horseradish peroxidase (purchased from santa cluz), and colored using ECL reagent, and finally, developed.

Figure 4:
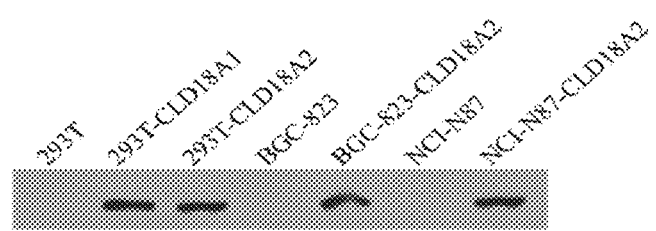
FIG. 4 is the results of the western blot assay of the cell lines stably expressing CLD18A1 and CLD18A2.

The Western blot results showed strips with molecule weight of about 28 kD in 293T cells transfected with CLD18A1 or CLD18A2 (i.e. 293T-CLD18A1, 293T-CLD18A2) and BGC-823 and NCI-N87 cells transfected by CLD18A2 (i.e. BGC-823-CLD18A2, NCI-N87-CLD18A2), but no strips in the untransfected empty cells (FIG. 4), indicating the successful construction of cell lines exogenously expressing CLD18A1 and CLD18A2.

3. Experiment Steps of Flow Cytometry Analysis of the Binding Profile of Each Cell Line with Anti-CLD18A2 Antibody Using a fluorescence activated cell sorter (FACS) (BD company, FACSCalibur), the respective binding ability of single-chain antibodies scFv-125, scFv-163 and scFv-175 with each of the following cell lines were tested.

The specific method is as follows:
1) 293T, 293T-CLD18A1, 293T-CLD18A1, 293T-CLD18A2, BGC-823, BGC-823-CLD18A2, NCI-N87, NCI-N87-CLD18A2 tumor cells at exponential growth phase were inoculated into 6 cm flat dish with a inoculation cell density about 90%, and incubated overnight at 37° C. in incubator.
2) The cells were digested by 10 mM EDTA, and collected by centrifugation at 200 g×5 min. The cells were resuspended in 1% phosphate buffer solution containing calf serum (NBS PBS) at a concentration of 1*10$^6$-1*10$^7$/ml), and added into cytometric pipe at 100 ul/pipe.
3) Centrifuged at 200 g for 5 min, and the supernatant were discarded.
4) The antibodies to be tested, scFv-125, scFv163 and scFv-175 were added, and simultaneously using unrelated antibodies as the negative control with final concentration of antibody of 20 μg/ml, and 100 ul of antibody in each pipe. Then they were left on Ice bath for 45 minutes.
5) Each pipe was added 2 ml 1% NBS PBS, centrifuged at 200 g for 5 min twice.
6) Supernatant was discarded. 1:50 diluted FITC-labeled goat anti-human antibody (from shanghai KangChen Bio-tech Inc), 100 ul per tube was added, and then put on ice bath for 45 minutes.

7) Each pipe was added 2 ml 1% NBS PBS, centrifuged at 200 g for 5 min twice.

8) The supernatant was discarded, and the pellet was resuspended in 300 ul 1% NBS PBS, detected by flow cytometry.

9) Flow Cytometer data analysis software WinMDI 2.9 was used to analyze the data.

Figure 5:
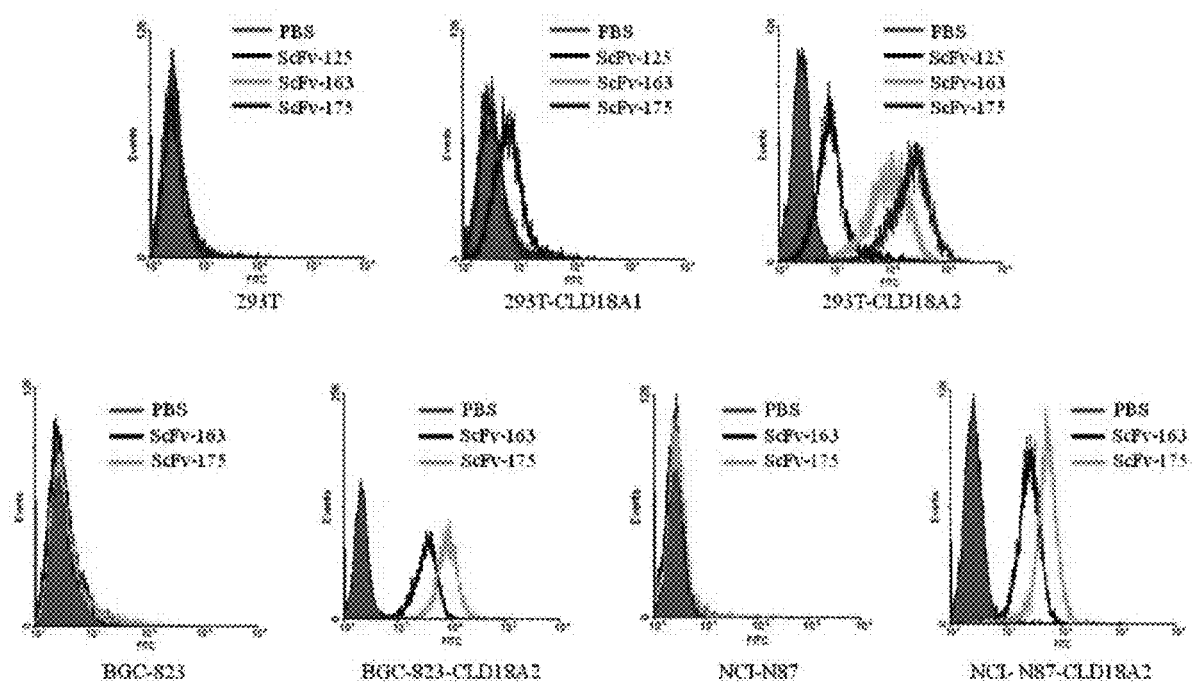
FIG. 5 is flow cytometric detection of the binding specificity of CLD18A2 single-chain antibody with CLD18A1 and CLD18A2.

The flow cytometry results showed that the single-chain antibody scFv-125 can not only bind to CLD18A1 stably expressed 293T cells but also CLD18A2 stably expressed 293T cells (FIG. 5), indicating that this single-chain antibody lacks binding specificity for CLD18A2. Luckily, single-chain antibody scFv-163 and scFv-175 can specifically recognize the 293T stably expressing CLD18A2, not bind to 293T cells stably expressing CLD18A1, which indicates that these two single-chain antibodies can specifically recognize CLD18A2. Furthermore, these two single-chain antibodies can also specifically recognize BGC-823 or NCI-N87 cell lines stably transfected with CLD18A2, but do not bind to the BGC-823 or NCI-n87 cells not transfected with CLD18A2.

Figure 2:
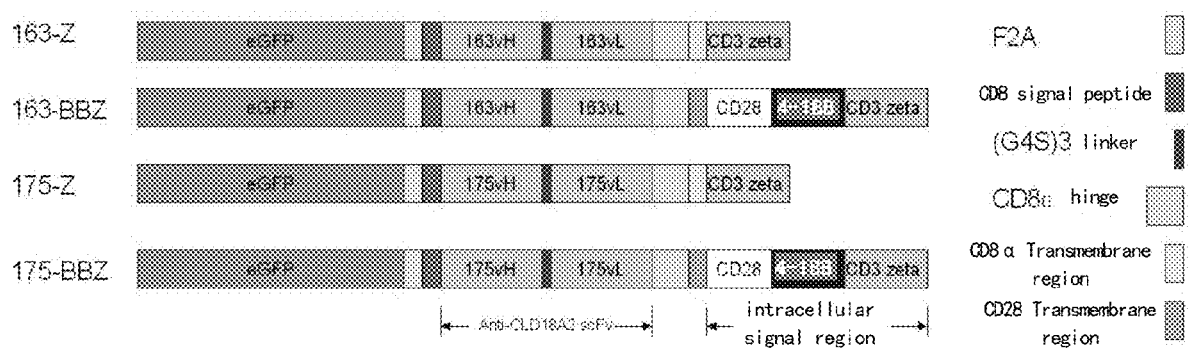
FIG. 2 is a schematic diagram of the connection sequence of each part of the chimeric antigen receptor. "(G4S)3 linker" in FIG. 2 is set forth in SEQ ID NO: 26.

Example 3 Construction of Lentiviral Plasmids Expressing Chimeric Antigen Receptor Proteins Encoded by the Nucleic Acids of the Present Invention, and Virus Packaging Table 1 explains the connection sequence of the exemplary chimeric antigen receptors of the present invention, the connection may also be seen in FIG. 2.

(2) The Nucleic Acid Sequence of Other Parts of the Chimeric Antigen Receptor

Other part of anti-CLD18A2 chimeric antigen receptor protein except scFv(CLD18A2-163, CLD18A2-175) were obtained by PCR using the sequences SEQ ID NOs: 18 and 21 disclosed in CN 201310164725.X.

Wherein the eGFP-F2A sequence was obtained by PCR amplification using plasmid of SEQ ID NO:18 described in the patent application number 201310164725.X as template and SEQ ID NOs: 11 and 12 as primer pair.

Obtaining CD8-CD3ζ (Z) and CD28a-CD28b-CD137-CD3ζ (28BBZ): CD8-CD3ζ(Z) and CD28a-CD28b-CD137-CD3ζ(28BBZ) fragments were respectively obtained by PCR amplification using scFv(GPC3)-CD8-CD3ζ(SEQ ID NO:18 in patent application 201310164725.X) and scFv(GPC3)-CD28a-CD28b-CD137-CD3ζ (SEQ ID NO:21 in patent application 201310164725.X) as templates and SEQ ID NOs: 13 and 14 as primer pair.

SEQ ID NO: 18 in 201310164725. X is corresponding to SEQ ID NO: 23 in the present invention The SEQ ID NO: 21 in 201310164725. X is corresponding to SEQ ID NO: 24 in the present invention.

2, Splicing of Nucleic Acid Fragments

The eGFP-F2A nucleic acid fragment obtained as mentioned previously, scFv (CLD18A2-163) or scFv (CLD18A2-175) nucleic acid fragments of equal molar, and CD8-CD3ζ (Z) or CD28a-CD28b-CD137-CD3ζ (BBZ) nucleic acid fragments of equal molar were subjected to three-fragment splicing as shown in FIG. 2 and PCR. The splicing conditions were as follows: predenaturation at 94° C. for 4 min; denaturation at 94° C. for 40 s; annealing at 60° C. for 40 s; extending at 68° C. for 140 s, 5 cycles, and then

| Chimeric antigen receptor | Extracellular binding region-transmembrane region-intracellular signal region 1-intracellular signal region 2, etc |
|---|---|
| CLD18A2-δZ | scFv(CLD18A2)-CD8-CD3δzeta (negative control) |
| CLD18A2-163-Z | scFv(CLD18A2-163)-CD8-CD3 zeta |
| CLD18A2-175-Z | scFv(CLD18A2-175)-CD8-CD3 zeta |
| CLD18A2-163-28BBZ | scFv(CLD18A2-163)-CD28a-CD28b-CD137(i.e. 4-1BB)-CD3 zeta |
| CLD18A2-175-28BBZ | scFv(CLD18A2-163)-CD28a-CD28b-CD137-CD3 zeta |

1. Amplification of Nucleic Acid Fragments (1) Amplification of scFv (CLD18A2-163, CLD18A2-175) sequences Using v5-scFv-163-fc plasmid as template, in the primer pair, the forward primer (SEQ ID NO: 7) comprises part of 2A sequence and the reverse primer (SEQ ID NO: 8) comprises part of CD8 hinge sequence. ScFv (CLD18A2-163) was obtained by PCR amplification. In the same way, using the v5-scFv-175-Fc plasmid as template, scFv (CLD18A2-175) was obtained by PCR amplification, using primer pair wherein the forward primer comprises part of 2A sequence (SEQ ID NO: 9) and the reverse primer (SEQ ID NO: 10) comprises part of the CD8 hinge sequence.

overall extension at 68° C. for 10 min. After addition of DNA polymerase and forward primer (SEQ ID NO:11) and reverse primer (SEQ ID NO: 14), the PCR amplification were done for 30 cycles, and the amplification conditions were: pre-denaturation at 94° C. for 4 min; denaturation at 94° C. for 40 s; annealing at 60° C. for 40 s; extension at 68° C. for 140 s, for 30 cycles; and then overall extension at 68° C. for 10 min. The fragments obtained after the amplification are as follows (Table 2):

eGFP-scFv(CLD18A2)-163-Z (SEQ ID NO:15, 19),
eGFP-scFv(CLD18A2)-163-BBZ (SEQ ID NO: 16, 20),
eGFP-scFv(CLD18A2)-175-Z (SEQ ID NO: 17, 21),
eGFP-scFv(CLD18A2)-175-BBZ (SEQ ID NO: 18, 22).

Figure 6:
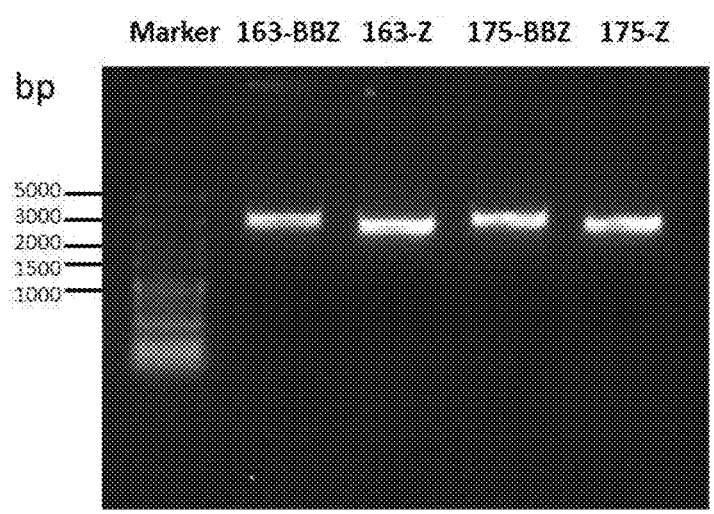
FIG. 6 is the electrophoresis identification of a spliced chimeric antigen receptor.

The results identification where shown in FIG. 6.

TABLE 2

The sequences in the present invention

| Sequence | Description |
|---|---|
| SEQ ID NO: 1 | Nucleic acid sequence encoding CLD18A2 single chain antibody 125 |
| SEQ ID NO: 2 | Amino acid sequence of CLD18A2 single chain antibody 125 |

TABLE 2-continued

The sequences in the present invention

| Sequence | Description |
| --- | --- |
| SEQ ID NO: 3 | Nucleic acid sequence encoding CLD18A2 single chain antibody 165 |
| SEQ ID NO: 4 | Amino acid sequence of CLD18A2 single chain antibody 163 |
| SEQ ID NO: 5 | Nucleic acid sequence encoding CLD18A2 single chain antibody 175 |
| SEQ ID NO: 6 | Amino acid sequence of CLD18A2 single chain antibody 175 |
| SEQ ID NO: 7~14 | Primer sequences |
| SEQ ID NO: 15 | Nucleic acid sequence encoding chimeric antigen receptor protein CLD18A2-163-Z |
| SEQ ID NO: 16 | Nucleic acid sequence encoding chimeric antigen receptor protein CLD18A2-163-28BBZ |
| SEQ ID NO: 17 | Nucleic acid sequence encoding chimeric antigen receptor protein CLD18A2-175-Z |
| SEQ ID NO: 18 | Nucleic acid sequence encoding chimeric antigen receptor protein CLD18A2-175-28BBZ |
| SEQ ID NO: 19 | Nucleic acid sequence encoding chimeric antigen receptor protein CLD18A2-163-Z |
| SEQ ID NO: 20 | Amino acid sequence of chimeric antigen receptor protein CLD18A2-163-28BBZ |
| SEQ ID NO: 21 | Amino acid sequence of chimeric antigen receptor proteinCLD18A2-175-Z |
| SEQ ID NO: 22 | Amino acid sequence of chimeric antigen receptor protein CLD18A2-175-28BBZ |
| SEQ ID NO: 23 | scFv(GPC3)-CD8-CD3ζ (SEQ ID NO: 18 in 201310164725.X) |
| SEQ ID NO: 24 | scFv(GPC3)-CD28a-CD28b-CD137-CD3ζ (SEQ ID NO:21 in 201310164725.X) |

3. Lentiviral Plasmid Vector Construction Method

As an example, the vector system used for constructing the lentiviral plasmid vector of the present invention belongs to a third generation self-inactivating lentivirus vector system, which comprises three plasmids, namely, psPAX2 encoding Gag/Pol protein and Rev protein (purchased from addgene); envelope plasmid PMD2.G encoding VSV-G protein (purchased from addgene); and recombinant expression vector encoding target gene CAR which is based on empty vector PWPT-eGFP (purchased from addgene)

In the empty vector pWPT-eGFP, the elongation factor-1 alpha (EF-1α) promoter regulates the enhanced green fluorescent protein (eGFP), while in the recombinant expression vector encoding target gene CAR, the co-expression of eGFP and CAR is realized via ribosome skipping sequence 2A (shortened as "F2A") from food-and-mouth disease virus (FMDV). F2A is a core sequence from FMDV 2A (or referred to as "self-splicing polypeptide 2A"), which has the "self-splicing" function of 2A, and can realize the co-expression of both upstream and downstream genes. Due to the high splicing efficiency, the highly balanced expression of upstream and downstream genes and the short sequence of itself, 2A provided an effective and feasible strategy for constructing polycistronic vector for gene therapy. In particular, this sequence is often used in the immune therapy based on chimeric antigen receptor gene modified T lymphocyte, to realize the co-expression of the target gene and GFP or eGFP, therefore CAR expression can be indirectly detected by detecting GFP or eGFP.

According to the present example, a lentivirus expression vector which co-expresses eGFP and a specific CAR linked by F2A was constructed, collectively, referred to as pWPT-eGFP-F2A-CAR (FIG. 1). The target gene eGFP-F2A-CAR obtained in step 2 (see 1(2) in Example 3, and the element following F2A is called as CAR for short) was digested by restriction endonucleases MluI and SalI, linked into a pWPT vector digested in the same way so as to construct a lentiviral vector expressing each chimeric antigen receptor. After the successfully constructed vector was confirmed by MluI and SalI digestive identification and sequencing, it can be subjected to lentivirus packaging. As previously mentioned, the eGFP-F2A-CAR was transcribed into a mRNA, but finally into two peptide chains as eGFP and anti-CLD18A2 chimeric antigen receptor. In the guidance of the CD8α signal peptide, the anti-CLD18A2 chimeric antigen receptor would locate on cell membrane.

The obtained vectors comprising target CAR are as follows:
pWPT-eGFP-F2A-scFv(CLD18A2)-163-Z;
pWPT-eGFP-F2A-scFv(CLD18A2)-163-BBZ;
pWPT-eGFP-F2A-scFv(CLD18A2)-175-Z;
pWPT-eGFP-F2A-scFv(CLD18A2)-175-BBZ.

4. Packaging Lentivirus by Plasmid Transfection of 293T

HEK-239T cells (ATCC: CRL-11268) cultured to 6-10 generations were inoculated at a density of 6×10$^6$ in 10 cm petri dish, incubated at 37° C., under 5% $CO_2$ overnight, preparing for transfection. The culture medium was DMEM (purchased from PAA company) with 10% fetal calf serum (purchased from PAA company). The next day, the culture medium was replaced with serum-free DMEM at about 2 hours before transfection.

The transfection steps were as follows:

4.1 20 g empty plasmids pWPT-eGFP (mock control) or 20 μg individual target gene plasmid pWPT-eGFP-F2A-CAR, together with 15 μg of packaging plasmid PAX2 and 6 μg envelope plasmid pMD2.G were dissolved into 500 μL MillQ water, and uniformly mixed.

4.2 62 μL of 2.5M $CaCl_2$) (purchased from Sigma company) was added dropwise, and mixed homogenously at 1200 rpm/min vortex, 4. 3 Finally, 500 μL of 2×HeBS (80 mM NaCl, 10 mM KCl, 1.5 mM $Na_2HPO4•2H_2O$, 12 mM glucose, 50 mM Hepes (purchased from Sigma), pH7.05, sterilization with a 0.22 um filter) was added dropwise, and mixed homogenously at 1200 rpm/min for 10 s.

4.4 Immediately added into the petri dish dropwise, slightly shaken, incubated at 37° C. and 5% $CO_2$. Cultured for 4-6 h, the culture medium was replaced with DMEM containing 10% fetal calf serum.

Transfection efficiency (ie, the proportion of cells with green fluorescence) was observed the next day of the transfection, and ~80% positive transfection efficiency indicated successful transfection experiment. After 48 h or 72 h of transfection, a 0.45 μm filter (purchased from Millipore Company) was used to filter and collect the virus, and centrifuged by Beckman Optima L-100 XP ultracentrifuge at 28,000 rpm, 4° C. for 2 hours, and the centrifuged supernatant was discarded. The precipitate obtained by centrifugation was resuspended with Quantum 007 culture solution (purchased from PAA Company) at 1/10-1/50 volume of the stock solution, packed at 100 μL/pipe and frozen at −80° C., waiting for virus titration or infecting T lymphocyte.

5. Determination of Titer of the Lentivirus Packed with Mock or eGFP-F2A-CAR

At Day 1, 293T cells were inoculated to a 96-well culture plate at $1*10^5$/ml, with 100 μL/well, incubated at 37° C. and 5% $CO_2$. The culture medium is DMEM medium containing 10% fetal calf serum. At day 2, 50 μL/well culture supernatant was discarded, and 504/well fresh culture medium was added, which contains polybrene at a final concentration of 6 μg/ml, and incubated at 37° C., 5% $CO_2$ for 30 min. 10 μL/well of virus stock solution or 1 μL/well of concentrated virus solution was added, diluted for 5 times, with 4 gradients, in duplicate. Incubated at 37° C. 5% $CO_2$ After 48 hours of infection, the flow cytometry was used for detecting eGFP preferably with positive rate at 5-20% of the cell number, calculated as titer (U/ml)=positive efficiency×dilution times×100×$10^4$. The titers of the above mentioned viruses packaged by the calcium phosphate transfection method, comprising MOCK (i.e. the empty vector control) and each eGFP-F2A-CAR were all at about 0.5-2*$10^6$ U/mL. Virus titer measured after concentration was about $2×10^7$ U/mL.

Example 4 Recombinant Lentivirus Infection of CTL Cells

Human peripheral blood mononuclear cells (provided by Shanghai Blood Center) were obtained from healthy human peripheral blood through density gradient centrifugation method. CTL cells were obtained from peripheral blood mononuclear cells by negative sorting method with CTL cell magnetic beads (purchased from Stem Cell Technologies), and the sorted CTL cells were subjected to flow cytometry to determine the purity of the CTL cells. CTL positive rate≥95% was preferred for next operation. Quantum 007 lymphocyte culture medium (purchased from PAA company) was added at a density of about $1×10^6$/ml for culturing, and magnetic beads (Invitrogen company) coated with both anti-CD3 and CD28 antibodies, at 1:1 cell:magnetic bead ratio, and recombinant human IL-2 with a final concentration of 100 U/ml (purchased from Shanghai Huaxin High Biotechnology Inc.) were added for stimulating and culturing for 24 h. Then the above recombinant lentivirus were used to infect the CTL cells at MOI≈5. The infected cells were subjected to passage at a density of $5*10^5$/ml every other day, while recombinant human IL-2 with a final concentration of 100 U/ml was supplemented to the lymphocyte culture medium.

At the 8$^{th}$ day of culture, each different chimeric antigen receptor expression in infected CTL cells was tested by flow cytometry. Because eGFP and CAR were co-expressed, the cells detected to be eGFP positive were the positive cells expressing chimeric antigen receptors. Non-infected T lymphocytes were taken as negative control, and the positive rate of the virus expressing different chimeric antigen receptors infecting CTL cells were shown in table 3. The positive rate results showed that lentivirus infection method can obtain CAR$^+$ CTL cells with certain positive rate.

After respectively infected and packaged with different chimeric antigen receptors, the CTL cells were passaged at cell density of $5*10^5$/ml and counted, and IL 2 (final concentration of 100 U/ml) was added to the passage cell culture solution. At 11$^{th}$ day of culture, there is amplification of about 20-40 times, indicating that the CTL cells expressing different chimeric antigen receptors have the ability to amplify in vitro, thus ensuring subsequent in-vitro toxicity tests and in-vivo experiments.

Example 5 In Vitro Toxicity Effect Assay for the Cells Expressing Chimeric Antigen Receptor The materials used in the in-vitro toxicity experiment are as follows:

The 293T and gastric cancer cell lines as shown in table 4 were used as target cells. The effector cells were CTLs that were in vitro cultured for 12 days as verified in example 4, and confirmed by FACS that they were chimeric antigen receptor expression positive (noted as CAR$^+$, chimeric antigen receptor positive). The effect:target ratios, upon different conditions were 3:1, 1:1, and 1:3, the number of the target cells was 10000/well. According to different effect:target ratio, each group set for five repeated wells, and the average value in 5 repeated wells was taken into count. The detection time was the 18th hour.

Wherein each experiment group and each control group were as follows:

Each experiment group: Each target cell+CTL expressing different chimeric antigen receptors, Control group 1: target cell with maximum release of LDH Control group 2: Target cell with spontaneous release of LDH Control group 3: effector cells with spontaneous release of LDH.

Detection method: Carried out with CytoTox 96 non-radioactive cytotoxicity assay kit (Promega company). The method was a detection method based on colorimetric method, and can replace $^{51}$Cr release assay. CytoTox 96® assay quantitatively determines lactate dehydrogenase (LDH). LDH is a stable cytoplasmic enzyme, is released during cell lysis, whose release profile is substantially the same as the release profile of $^{51}$Cr in radioactivity analysis. The released LDH would be in the culture supernatant and can be detected by a 30-minute coupled enzyme reaction. In enzyme reaction, LDH can transfer a tetrazole salt (INT) into red Formazan. The red product is directly proportional to the number of lyzed cells. Refer to the instruction of CytoTox 96 non-radioactive cytotoxicity assay kit for details.

TABLE 3

| CTL cells transfected with the following CAR | eGFP possitive rate of the CTL cells |
| --- | --- |
| Mock(empty vector control) | 56% |
| CLD18A2-Z, fused and expressing 163 single chain antibody | 51% |
| CLD18A2-28BBZ, fused and expressing 163 single chain antibody | 54% |
| CLD18A2-Z, fused and expressing 175 single chain antibody | 52% |
| CLD18A2-28BBZ, fused and expressing 175 single chain antibody | 55% |

The cytotoxicity calculation formula is as follows:

$$\text{cytotoxicity \%} = \frac{\text{Experimental group} - \text{Control group2} - \text{Control group 3}}{\text{Control group 1} - \text{Control group2}} \times 100\%$$

As specifically shown in table 4 and table 5, the present CTLs expressing chimeric antigen receptor (fusion expressing single chain antibody 163 or 175) CLD18A2-Z CAR$^+$ and CLD18A2-28BBZ CAR$^+$ have significant killing effect on 293T cells with high expression of CLD18A2, but not on the 293T cells expressing CLD18A1, which indicates that they can selectively kill the cells with CLD18A2. Furthermore, the present CTLs expressing chimeric antigen receptor CLD18A2-Z CAR$^+$ and CLD18A2-28BBZ CAR$^+$ have also significant killing effect on two gastric cancer cell lines BGC-823 and NCI-N87 with high expression of CLD18A2 (see table 4 and table 5), and it showed effect:target ratio dependency, that is, the higher the effect:target ratio, the stronger the cytotoxicity. However, there was no cytotoxicity to BGC-823 and NCI-N87 that do not express CLD18A2.

The data of the effect-target dependency further indicated that the present CTL of anti-CLD18A2 chimeric antigen receptor showed specific cytotoxicity to gastric cancer cells with high CLD18A2 expression.

Comparatively, the CTL transfected by MOCK plasmid (empty plasmid vector pWPT-eGFP not carrying CLD18A2-CAR) showed quite low cytotoxicity to above 3 cell lines with high CLD18A2 expression. The data of cytotoxicity to cell lines with high CLD18A2 expression exhibits significant difference between the CTL transfected by MOCK plasmid and the CTL expressing the present anti-CLD18A2 chimeric antigen receptor.

The above results showed that the chimeric antigen receptor constructed by choosing the single-chain antibody against CLD18A2 can selectively kill target cells with high CLD18A2 expression. In addition, from the cytotoxicity data, CAR T of CLD18A2-28BBZ has stronger cytotoxicity to cells expressing CLD18A2 than CART of CLD18A2-Z.

TABLE 4

Cytotoxicity of CAR T cells expressing single-chain antibody 163

| | CLD18A2-28BBZ different effect:target ratio | | | CLD18A2-Z different effect:target ratio | | | MOCK different effect:target ratio | | |
|---|---|---|---|---|---|---|---|---|---|
| CYTOTOXICITY (%) | 3:1 | 1:1 | 1:3 | 3:1 | 1:1 | 1:3 | 3:1 | 1:1 | 1:3 |
| 293T-CLD18A1 | 8.9 | 7.3 | 6.2 | 5.2 | 4.8 | 4.3 | 3.1 | 2.3 | 2.6 |
| 293T-CLD18A2 | 50 | 38.9 | 16.7 | 30.4 | 20.8 | 13.6 | 5.4 | 4.4 | 4.5 |
| BGC-823-CLD18A2 | 62.7 | 44.7 | 16.1 | 38.9 | 25.8 | 10.5 | 5.7 | 4.8 | 4.3 |
| BGC-823 | 5.8 | 5.5 | 4.8 | 5.2 | 4.6 | 5.5 | 2.8 | 3.5 | 3.8 |
| NCI-N87-CLD18A2 | 61.3 | 52.5 | 13.6 | 42.8 | 26.3 | 7.7 | 6.1 | 5.2 | 4.7 |
| NCI-N87 | 4.6 | 5.1 | 5.9 | 3.6 | 3.5 | 4.5 | 3.9 | 4.2 | 3.1 |

TABLE 5

Cytotoxicity of CAR T cells expressing single-chain antibody 175

| | CLD18A2-28BBZ different effect:target ratio | | | CLD18A2-Z different effect:target ratio | | | mock different effect:target ratio | | |
|---|---|---|---|---|---|---|---|---|---|
| cytotoxicity (%) | 3:1 | 1:1 | 1:3 | 3:1 | 1:1 | 1:3 | 3:1 | 1:1 | 1:3 |
| 293T-CLD18A1 | 8.6 | 7.3 | 6 | 5.4 | 4.8 | 2.7 | 2.4 | 1.5 | 1.4 |
| 293T-CLD18A2 | 57.5 | 41 | 15 | 35.2 | 25.7 | 13.2 | 5.6 | 2.3 | 1.6 |
| BGC-823-CLD18A2 | 69.4 | 45.4 | 17.2 | 43.5 | 24.6 | 8.7 | 9.2 | 6.9 | 3.4 |
| BGC-823 | 4.5 | 4.8 | 5.2 | 3.8 | 3.9 | 4.5 | 2.5 | 3.5 | 2.8 |
| NCI-N87-CLD18A2 | 68.2 | 44.2 | 16.3 | 41.5 | 28.2 | 10.2 | 10.1 | 8.2 | 3.3 |
| NCI-N87 | 5.2 | 2.9 | 3.9 | 4.2 | 3.3 | 4.5 | 2.5 | 3.2 | 4.3 |

DISCUSSION

At present, CAR T cells have become a potential therapeutic means. However, many tumors, such as gastric cancer, do not have reports about CAR T cell therapy. There is research showing that CLD18A2 may be a specific marker of stomach tissue, therefore, it can also be a therapeutic target for tumor such as stomach cancer. However, at present, only the monoclonal antibody has been considered as the candidate drug with CLD18A2 as the therapeutic target, and whether it can be successfully used for the corresponding tumor treatment or not is not yet known. Therefore, it is necessary to find new treatment means. Considering the tissue specificity of CLD18A2, tithe present invention contemplates that if targeted therapy can be performed with CAR T cells, a novel antitumor formulation can be expected. However, it is known that the CLD18A2 antigen is a tightly-connected protein, whether it can contact with CAR T cells and induce the killing of the corresponding target cells is not known. In addition, as the protein spatial conformation is very crucial to the whole protein, many monoclonal antibody lose their antigen binding activity or specificity when evolving into single-chain antibodies. Fortunately, the inventors found that two single-chain antibodies (163 and 175) retained the antigen binding specificity of the monoclonal antibody. Further research shows that the CAR T cells composed of these two single-chain antibodies retained the selective killing effect on CLD18A2 positive cells. The results of the invention showed that CLD18A2 can truly be a CAR T cell therapy target; the CAR T cell against CLD18A2 is a novel candidate tumor treatment candidate means.

All documents mentioned in this disclosure are all incorporated herein by reference, as if each document is individually referred to as a reference. Furthermore, it should be understood that after reading the above teachings of the invention, those skilled in the art can make various variations or modifications to the present invention, these equivalent forms are also within the scope defined by the appended claims.

The invention claimed is:

1. A chimeric antigen receptor expressed on a surface of an immune effector cell, comprising an extracellular binding region, a transmembrane region, and an intracellular signal region, wherein the extracellular binding region comprises a protein which specifically recognizes CLD18A2, wherein the transmembrane region has a sequence comprising a sequence of transmembrane region and hinge region of CD8 or CD28, the intracellular signal region sequence is selected from the following: an intracellular signal region sequence of CD3ζ, FcεRIγ, CD27, CD28, CD137, CD134, or a combination thereof.

2. The chimeric antigen receptor according to claim 1, wherein the extracellular binding region comprises an amino acid sequence of any one of SEQ ID NOs.4 and 6.

3. The chimeric antigen receptor according to claim 1, wherein the chimeric antigen receptor comprises the extracellular binding region, the transmembrane region, and the intracellular signal region connected in the following sequence:
   the amino acid sequence of any one of SEQ ID NOs.4 and 6, CD8 and CD3ζ;
   the amino acid sequence of any one of SEQ ID NOs.4 and 6, CD8, CD137 and CD3ζ;
   the amino acid sequence of any one of SEQ ID NOs.4 and 6, transmembrane region of CD28, intracellular signal region of CD28 molecule and CD3ζ; or
   the amino acid sequence of any one of SEQ ID NOs.4 and 6, transmembrane region of CD28, intracellular signal region of CD28, CD137 and CD3ζ.

4. The chimeric antigen receptor according to claim 1, wherein the immune effector cells comprise: T lymphocytes, NK cells, or NK-T cells.

5. A nucleic acid encoding the chimeric antigen receptor according to claim 4.

6. An expression vector, comprising any one of the nucleic acids according to claim 5, wherein the expression vector is derived from lentivirus plasmid PWPT.

7. A virus, comprising the expression vector according to claim 6.

8. A genetically modified immune effector cell, transduced by nucleic acid according to claim 5, the expression vector according to claim 6, or the virus according to claim 7.

9. A genetically modified immune effector cell with a chimeric antigen receptor expressing on the surface thereof, wherein the amino acid sequence of said chimeric antigen receptor is selected from any one of the amino acid sequences of SEQ ID NOs: 19-22.

10. The genetically modified immune effector cell according to claim 9, wherein the immune effector cells comprise: T lymphocytes, NK cells, or NK-T cells.

* * * * *

UNITED STATES PATENT AND TRADEMARK OFFICE
CERTIFICATE OF CORRECTION

PATENT NO. : 12,098,199 B2  
APPLICATION NO. : 17/522284  
DATED : September 24, 2024  
INVENTOR(S) : Huamao Wang, Bo Song and Xiumei Cai Page 1 of 1

It is certified that error appears in the above-identified patent and that said Letters Patent is hereby corrected as shown below:

In the Claims

Column 60, Line 8, Claim 5:
Replace "claim 4" with --claim 1--.

Signed and Sealed this  
Second Day of September, 2025

Coke Morgan Stewart  
*Acting Director of the United States Patent and Trademark Office*